(12) United States Patent
Robertson et al.

(10) Patent No.: US 7,510,874 B2
(45) Date of Patent: Mar. 31, 2009

(54) STABLE CELL LINES EXPRESSING HERG1A AND HERG1B

(75) Inventors: Gail A. Robertson, Madison, WI (US); Eugenia M. Jones, Madison, WI (US); Jinling Wang, Pasadena, CA (US)

(73) Assignee: Wisconsin Alumni Research Foundation, Madison, WI (US)

(*) Notice: Subject to any disclaimer, the term of this patent is extended or adjusted under 35 U.S.C. 154(b) by 493 days.

(21) Appl. No.: 10/976,122

(22) Filed: Oct. 28, 2004

(65) Prior Publication Data

US 2005/0164379 A1    Jul. 28, 2005

Related U.S. Application Data

(60) Provisional application No. 60/515,158, filed on Oct. 28, 2003.

(51) Int. Cl.
| | |
|---|---|
| C12N 15/85 | (2006.01) |
| C12N 5/08 | (2006.01) |
| C07K 14/00 | (2006.01) |
| C07K 16/00 | (2006.01) |
| C07H 21/04 | (2006.01) |

(52) U.S. Cl. .................. 435/325; 435/366; 435/369; 530/350; 530/388.22; 536/23.1; 536/23.5

(58) Field of Classification Search .................. None
See application file for complete search history.

(56) References Cited

OTHER PUBLICATIONS

Alomone Labs, "ERG K+ Channels," Modulator 13:1-2 (2001).
Crociani, O., et al., "Cell Cycle-Dependent Expression of HERG1 and HERG1B Isoforms in Tumor Cells," The Journal of Biological Chemistry 278:2947-2955 (2003).
Curran, M.E., et al., "A molecular basis for cardiac arrhythmia: HERG mutations cause long QT syndrome," Cell 80:795-803 (1995).
Delisle, B.P., et al., "Biology of Cardiac Arrhymias Ion Chanel Protein Trafficking," Circulation Research Jun. 11, 2004:1418-1428.
He, J.Q., et al., "Reduction in density of transverse tubules and L-type Ca(2+) channels in canine tachycardia-induced heart failure," Cardiovascular Research 49:298-307 (2001).
Jones, E. M., et al., "HERG-1b Protein is Experssed in Cardiac Ventricular Myocytes," Scientific Sessions 2003.
Kupershmidt, S., et al., "A K+ channel splice variant common in human heart lacks a C-terminal domain required for expression of rapidly activating delayed rectifier current," J. Biol. Chem. 273:27231-27235 (1998).
Lees-Miller, J.P., et al., "Electrophysiological characterization of an alternatively processed ERG K+ channel in mouse and human hearts," Circ. Res. 81:719-726 (1997).
London, B., et al., "N- and C-terminal isoforms of HERG in the human heart," Biophysical J. (1998).
O'Leary, M.E., "Inhibition of Human Ether-A-Go-Go Potassium Channels by Cocaine," Molecular Pharmacology 59:269-277 (2001).
Roti Roti, E.C., et al., "Interaction with GM130 during HERG Ion Channel Trafficking," The Journal of Biological Chemistry 277:47779-47785 (2002).
Sanguinetti, M.C., et al., "Two components of cardiac delayed rectifier K+ current. Differential sensitivity to block by class III antiarrhythmic agents," J. Gen. Physiol. 96:195-215 (1990).
Sanguinetti, M.C., et al., "A mechanistic link between an inherited and an acquired cardiac arrhythmia: HERG encodes the IKr potassium channel," Cell 81:299-307 (1995).
Sanguinetti, M.C., et al., "Coassembly of K(V)LQT1 and minK (IsK) proteins to form cardiac I(Ks) potassium channel," Nature 384:80-83 (1996).
Trudeau, M.C., et al., "HERG, a Human Inward Rectifier in the Voltage-Gated Potassium Channel Family," Science 269:92-95 (1995).
Wang, J., et al., "Dynamic Control of Deactivation Gating by a Soluble Amino-Terminal Domain in HERGK+ Channels," J. Gen Phyiol. 115:749-758 (2000).
Wang, J., et al., "Regulation of Deactivation by an Amino Terminal Domain in Human Ether-a-go-go-related Gene Potassium Channels," J. Gen. Phyiol. 112:637-647 (1998).
Zhou, A., et al., "HERG channel dysfunction in human long QT syndrom. Intracellular transport and functional defects," J. Biol. Chem. 273:21061-21066 (1998).
Zhou, A., et al., "Properties of HERG channels stably expressed in HEK 293 cells studied at physiological temperature," Biophys. J. 74:230-241 (1998).
Jones E, et al., "Cardiac IKr channels minimally comprise hERG 1a and 1b subunits," J. Biol. Chem. 279:44690-44694 (2004).
London B, et al., "Two isoforms of the mouse ether-a-go-go-related gene coassemble to form channels with properties similar to the rapidly activating component of the cardiac delayed rectifier K+ current," Circ. Res. 81:870-878 (1997).
Ohya S, et al., "Functional and molecular identification of ERG channels in murine portal vein myocytes," Am. J. Physiol. Cell Physiol. 283:C866-877 (2002).
Pond L, et al., "Expression of distict ERG proteins in rat, mouse, and human heart. Relation to functional I(Kr) channels," J. Biol. Chem. 275:5997-6006 (2000).

*Primary Examiner*—Elizabeth C. Kemmerer
*Assistant Examiner*—Sandra Wegert
(74) *Attorney, Agent, or Firm*—Quarles & Brady LLP

(57) ABSTRACT

A line of cultured mammalian cells includes HERG1b subunits and optionally HERG1a subunits.

7 Claims, 2 Drawing Sheets

STABLE CELL LINES EXPRESSING HERG1A AND HERG1B

CROSS-REFERENCE TO RELATED APPLICATIONS

This application claims the benefit of U.S. Provisional Application No. 60/515,158, filed Oct. 28, 2003.

STATEMENT REGARDING FEDERALLY SPONSORED RESEARCH OR DEVELOPMENT

This invention was made with United States government support awarded by the following agency: NIH Grant Number HL55973. The United States government has certain rights in this invention.

BACKGROUND OF THE INVENTION

Ion channels expressed in the plasma membrane of excitable tissues (including heart) regulate the function of the tissues. Ion channels can comprise alpha, beta and auxiliary subunits. The alpha subunits are largely responsible for determining overall biophysical properties of the channels, such as ion selectivity, gating and drug sensitivity, whereas beta or auxiliary subunits modify these properties in important ways. Voltage-gated potassium channels comprise four alpha subunits that assemble into a pseudosymmetric array (MacKinnon, 1991), thereby providing the opportunity for heterogeneity by mixing of related subunits to form heterotetrameric channels (Christie et al., 1990; Isacoff et al., 1990). The potential for complexity and heterogeneity increases substantially when beta or auxiliary subunits are also present (England et al., 1995).

Cardiac $I_{Kr}$ is a rapidly-inactivating potassium current first identified by its sensitivity to the methanesulfonanilide drug E-4031 (Sanguinetti, M. C. and N. K. Jurkiewicz, 1990). Compared to all other known potassium currents, $I_{Kr}$ has a unique functional profile characterized by the suppression of current during depolarization and large, rebounding tail currents produced upon repolarization. Currents are suppressed during depolarization because channels open only briefly and then rapidly inactivate. Upon repolarization, channels recover rapidly from inactivation and revisit the open state. Because deactivation is slow, the channels linger in this highly stable open state and produce the resurgent current that is a hallmark of $I_{Kr}$. Moreover, the sensitivity to E-4031 and other antiarrhythmic drugs is unique to $I_{Kr}$.

Currents with comparable biophysical and pharmacological properties are produced when HERG1, a gene encoding an inwardly rectifying potassium channel that was cloned from human hippocampus (Warmke and Ganetzky, 1994), is transiently expressed in *Xenopus* oocytes, suggesting that HERG1 is a central component of the channels that give rise to the $I_{Kr}$ currents (Sanguinetti et al., 1995; Trudeau et al., 1995). Trudeau, M. C., et al., "HERG, a Human Inward Rectifier in the Voltage-Gated Potassium Channel Family," *Science* 269:92 (1995), incorporated by reference as if set forth herein in its entirety, described the HERG gene and also depicted the inwardly rectifying HERG currents and a gating model in the same paper.

Families with a form of inherited (familial) Long QT Syndrome (LQTS-2) have mutations the HERG1 gene (Curran et al., 1995). LQTS-2 is a life-threatening illness characterized by polymorphic ventricular arrhythmias known as torsades de pointes (Roden, 1993). Undiagnosed or untreated, LQTS often leads to sudden death by young adulthood. The expression studies of Trudeau et al. (1995), defining HERG as the primary component underlying $I_{Kr}$, thus explained the underlying cause of LQTS-2 as a loss of $I_{Kr}$.

More clinically prevalent than familial LQTS is an acquired form of the disease caused by block of $I_{Kr}$ currents by a surprising variety of drugs, including antiarrhythmic drugs such as dofetilide (Tikosyn®) (Snyders and Chaudhary, 1996), the antihistamines terfenadine (Seldane®) (Roy et al., 1996; Suessbrich et al., 1996) and astemizole (Hismanal®) (Zhou et al., 1999b), the gastric motility drug cisapride (Propulsid®) (Mohammad et al., 1997; Rampe et al., 1997), and cocaine (Zhang S, 2001). An estimated 1-8% of the general public is susceptible to acquired LQTS. Despite their therapeutic value, several of these drugs have been withdrawn from the market because of an unacceptable risk of torsades. As a result, to avoid the risk of torsades and the lost investment associated with withdrawal of a drug from the market, standard pharmaceutical industry practice today dictates that all pharmaceutics in development are screened against cultured cells that express HERG1 in the cell membranes with monitoring for changes in potassium channel behavior. Commercially available HERG-expressing cell lines express only HERG1a channel subunits that assemble into HERG1 channels.

While it is accepted that $I_{Kr}$ channels primarily contain HERG 1 subunits, the precise composition of these channels is unknown. The discovery of alternative HERG1a and HERG1b transcripts encoded by the HERG1 gene in human heart (Lees-Miller et al., 1997; London et al., 1997; Kupershmidt et al., 1998; London et al., 1998, each incorporated by reference as if set forth herein in its entirety), raised the possibility that alpha subunits other than HERG1a contribute to the $I_{Kr}$ channels.

The proteins encoded by the HERG1a and HERG1b transcripts differ only at their amino termini, as shown in the attached Sequence Listing. The longer amino terminus of HERG1a confers slow deactivation; the shorter amino terminus of HERG1b confers rapid deactivation, relative to HERG1a. When transiently expressed together in a heterologous *Xenopus* oocyte system, the two subunits assemble to form heteromeric channels that produce currents with unique, intermediate deactivation properties that cannot be explained by the algebraic summation of two homomeric populations of channels. HERG1a DNA and amino acid sequences (SEQ ID NO:1 and 2, respectively) can be found at GenBank Accession No. NM_000238, and HERG1b DNA and amino acid sequences (SEQ ID NO:3 and 4, respectively) can be found at GenBank Accession No. NM_172057). The understanding of the art in this regard is presented in London, B. et al., "Two Isoforms of the Mouse Ether-a-go-go-Related Gene Co-assemble to Form Channels With Properties Similar to the Rapidly Activating Component of the Cardiac Delayed Rectifier K$^+$ Current," *Circ. Res.*, 81:870 (1997), which is incorporated by reference as if set forth herein in its entirety.

Although HERG1b transcripts have been observed in human heart tissue, until now there was no convincing evidence for the existence in the heart of HERG1b protein, nor was there a consensus as to whether HERG1a and HERG1b channel subunits co-assemble in the heart in vivo. It has heretofore been presumed that HERG channels in cardiac myocytes are uniformly formed of HERG1a subunits and a host of such HERG1a-containing cell lines are available for testing, as described. Even so, the potassium ion channel behavior of HERG1a-containing cell lines does not fully match the behavior of $I_{Kr}$ currents observed in cardiac myocytes. Additionally, from the prior work in *Xenopus* oocytes one cannot predict co-assembly of HERG1a and HERG1b subunits, let alone production of an $I_{Kr}$ current, in the membranes of mammalian cells, particularly upon heritable maintenance and expression of HERG1a and HERG1b in such cells. Understanding cardiac $I_{Kr}$ physiology and the disease mechanisms of HERG-linked congenital and acquired LQTS necessitates approximating the native state in heterologous systems as closely as possible. It would be desirable to provide improved cell lines for pharmacologic testing, where the improved cell lines mirror the potassium ion channel behavior and subunit composition found in cardiac myocytes.

BRIEF SUMMARY OF THE INVENTION

ERG is understood by the skilled person to refer to the ether-a-go-go related gene, and ERG to the corresponding protein, identified in various mammalian, non-mammalian, and non-vertebrate species. HERG and HERG refer to the human ERG homolog, and corresponding protein, respectively. Reference herein to HERG refers to the human ether-a-go-go related gene while ERG indicates the homolog in lower mammals. When discussing an anti-ERG antibody, the applicants intend that the antibody reacts across species and interacts with the ERG protein (or ERG1a or ERG1b subunits) from both human and non-human animals. There is very close sequence similarity between the genes and the encoded proteins in higher and lower mammals, as well as interspecies cross-reactivity of isoform-specific antibodies.

The present invention relates to the direct demonstration by the inventors that both the HERG1a and HERG1b proteins are present in the cell membranes of heart tissue of human and non-human animals, and further that when both proteins are stably expressed in a mammalian cell line, a single antibody raised specifically against either the HERG1b or HERG1a subunits co-precipitates both the HERG1a and the HERG1b subunits. The inventors have demonstrated that ERG1a and ERG1b subunits of non-human animals are also expressed in non-human animal cardiac tissue.

Further, HERG1a and HERG1b expression in a heterologous mammalian cell system produced current with the characteristic hallmark pharmacological and biophysical properties of native $I_{Kr}$ channels, namely sensitivity to a methanesulfonanilide drug, suppression of current during depolarization, rebounding tail currents produced upon repolarization. These hallmarks, and the ability to distinguish an $I_{Kr}$ current from a non-$I_{Kr}$ current, are understood by the skilled artisan familiar with the papers by Sanguinetti, M C and Jurkiewicz (1990), Sanguinetti, M C et al. (1995) and by Trudeau, M C, et al. (1995), each incorporated by reference herein as if set forth in its entirety.

A first aspect of the invention follows from these demonstrations. In accord with the first aspect, the invention is summarized in that cardiac $I_{Kr}$ can be recapitulated in a line of cultured mammalian cells, notably human cells, having a cell membrane that comprises HERG potassium ion channels having HERG1a and HERG1b subunit components, wherein the HERG1a and HERG1b subunit components are heterologous to the line of cultured cells where the cultured cells do not contain the subunit components until polynucleotides encoding the components are provided in the cells. A cell line thus produced is useful for screening of a pharmacologic agent for an effect on potassium ion channel behavior, in the manner that cell lines comprising HERG1a channels alone are now used. A heterologous subunit is expressed in the line of cultured cells as a result of stable and heritable transfer of a subunit-encoding polynucleotide into cells used to produce the cell line. Relatedly, a line of cultured cells having a HERG1b subunit component without a HERG1a subunit component, wherein the HERG1b subunit component is heterologous to the cells, is also useful for evaluating the potassium ion channels formed in, and the membrane potential of, such cells, as a tool to evaluate ion channels in patients having a truncated HERG1a subunit or no HERG1a subunit and to screen and develop compounds that may be effective in enhancing HERG1b surface expression and thus rescuing the mutant phenotype. While it will be appreciated that mammalian cell lines comprising other ERG orthologs can be prepared and used as described herein, such cells are of less commercial interest than cells expressing HERG, as it is the behavior of the human ion channels in human cells that is of interest when screening prospective new drugs for use in humans. However, such cells could find utility in screening of veterinary pharmaceuticals for possible effects upon ERG ion channels in non-human animals. While the application is generally directed to HERG-expressing cells, it is understood that ERG-expressing cells are also within the scope of the disclosure.

A second aspect of the invention is summarized in that a method for screening a pharmacologic agent for an effect on potassium ion channel behavior includes the steps of (1) establishing a baseline potassium ion channel behavior of a line of cultured cells having a cell membrane that comprises HERG potassium ion channels having HERG1a and HERG1b subunit components, (2) exposing the line of cultured cells to a pharmacologic agent, (3) determining the potassium ion channel behavior of the exposed cells, (4) comparing the potassium ion channel behavior of the exposed cells to the baseline potassium ion channel behavior, and (5) determining whether the pharmacologic agent affects the potassium ion channel behavior of the cells. Ion channel behavior can be assessed using any conventional electrophysiological approach such as a square voltage clamp protocol or an action potential clamp protocol. The latter is advantageous as it approximates the physiological behavior of the ion channels in cardiac tissue, particularly with regard to the opening and closing of the channels, and thereby yields more meaningful information about the binding of a pharmacologic agent to an open channel and the associated risk to an individual.

In a related aspect, the invention is further summarized in that a method for establishing a line of cultured cells includes the steps of (1) introducing into an expression-component cell line one or more expression vectors containing polynucleotides that encode HERG1b (and, optionally, HERG1a) under the control of an upstream transcriptional promoter and an optional downstream polyA addition sequence under conditions favoring transcription of one or more transcripts from the vector and translation from the transcripts to yield HERG1a and HERG1b subunits for co-assembly into heterotetrameric HERG channels in the membranes of the cells, (2) selecting cells that express either the HERG1b subunit alone or the HERG1a and HERG1b subunits, and (3) expanding a single cell clone to establish the line of cultured cells. To confirm expression of the HERG1a and HERG1b in the cultured cell line, levels of HERG subunit expression can be evaluated in the line using biochemical or electrophysiological methods or both.

In still another related aspect, the invention is further summarized in that in the method for establishing a line of cultured cells, the polynucleotides that encode HERG1a and HERG1b are the published polynucleotides that encode conventional HERG1a and HERG1b, wherein such sequences are presented herein in SEQ ID NO:1 and SEQ ID NO:3. Optionally, additional related cell lines in keeping with the invention can be established by substituting for the conventional HERG1a- or HERG1b-encoding polynucleotides, or both, related polynucleotides carrying mutations known in the art to be associated with LQTS. The skilled artisan will appreciate that the evaluation of a pharmacologic agent can be customized for a particular individual if the HERG profile (protein sequences of the HERG1a and HERG1b subunits) in the tested line of cultured cells matches or substantially matches the HERG profile of the individual.

These findings have significant implications for N-terminal mutations that are causally associated with LQTS. Approximately 20% of LQTS-2 mutations reside in the N terminus of HERG1a, where they can truncate the protein, alter gating properties, and/or cause trafficking deficiencies. Since HERG1a and HERG1b are alternate transcripts produced by the HERG1 gene, mutations in exons encoding the HERG1a N-terminus are not likely to affect the production of wild-type HERG1b from this gene. These findings suggest the importance of screening LQTS patients for mutations in the HERG1b-specific exon and for assessing the disease mechanism of all mutations in heterologous expression systems in which HERG1a and HERG1b are co-expressed.

In another aspect, the invention relates to a polyclonal or monoclonal antibody specific for the ERG1b isoform. In this regard, the inventors have produced a polyclonal antibody specific for the ERG1b isoform. It is the only such antibody known to be in existence, and it is useful in many applications, especially for establishing and characterizing the cell lines of the invention and for localizing the ERG1b isoform in vivo. The anti-ERG1b antibody recognizes HERG1b (from humans) and ERG1b (from non-human species).

In a related aspect, the invention further relates to a polyclonal or monoclonal antibody specific for the ERG1a isoform, the antibody being raised against an epitope in the ERG1a subunit, where the epitope shares amino acid similarity with the ERG1b epitope used to produce the ERG1b antibody and has a Jameson-Wolf antigenic index greater than 1. A portion of ERG1a between amino acids 264 and 286, inclusive, has these attributes. Interestingly, the characteristics of this epitope are also found in the 1a/1b C-terminal epitope and the HERG1b N-terminal epitope, used to raise the ERG-KA antibody and the ERG1b antibody, respectively, but in no other contiguous ~20 amino acid long portion of the HERG1a or HERG1b protein. In particular, these regions are characterized by a first pair of basic amino acid residues (such as conservatively related arginine or lysine residues) spaced apart by a single residue and a second pair of adjacent basic residues separated from the aforementioned pair by three to six amino acid residues.

In another related aspect, the cultured cells of the invention can also be employed in a screen for anti-cancer HERG blocker drugs, since it has been reported that HERG channels are upregulated in tumor cells and that proliferation of tumor cells is blocked by HERG blockers (Crociani et al., 2003).

It is an object of the invention to provide a line of cultured cells for screening of pharmacologic agents for an effect on potassium ion channel behavior where the line of cells recapitulates native cardiac $I_{Kr}$ or the $I_{Kr}$ observed in cardiac cells having mutant HERG channels.

It is a feature of the invention that the cultured cells have a cell membrane that comprises HERG potassium ion channels having native or mutant HERG1a and HERG1b subunit components.

Other objects, advantages and features of the invention will become apparent upon consideration of the following description taken in conjunction with the accompanying drawings.

DETAILED DESCRIPTION OF THE INVENTION

Figure 1:
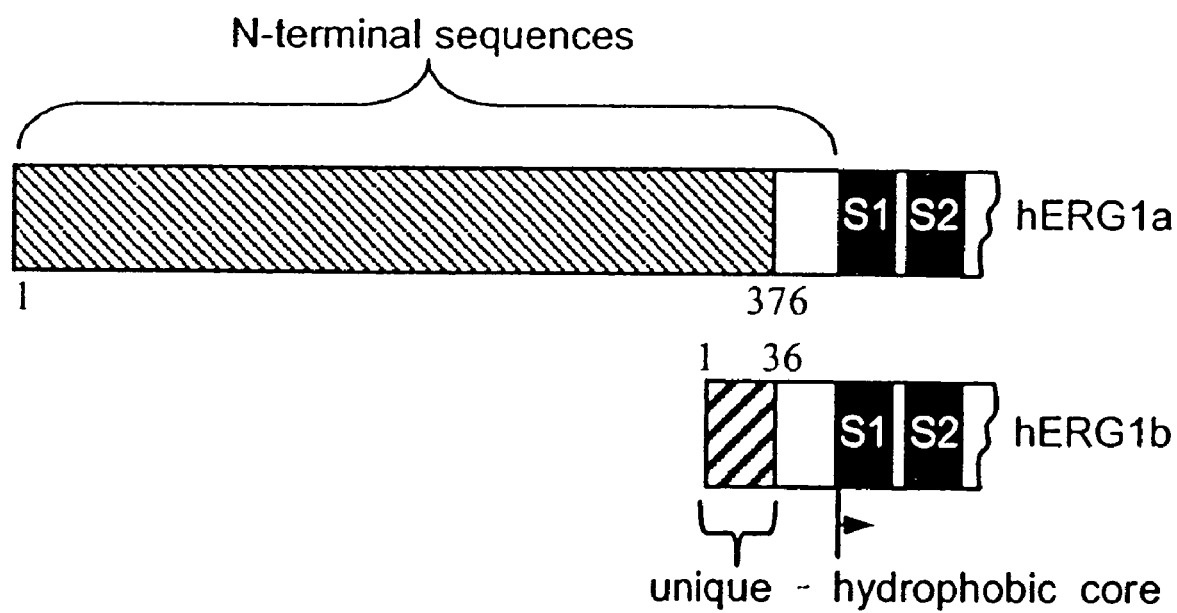
FIG. 1 illustrates the schematic topology of N-terminal regions of HERG1a and HERG1b proteins showing divergent N termini (hatched) and identical regions (white and black). Predicted molecular mass for ERG1a is 127 kD, and 90 kD for ERG1b.

Conventional or native HERG1a and HERG1b channel subunits are encoded by the HERG1 gene and arise as the result of differential splicing. The polynucleotide that encodes native HERG1a is published by NCBI and is presented herein at SEQ ID NO:1. The polynucleotide that encodes native HERG1b is published at http://www.ncbi.nlm.nih.gov/ and is presented herein at SEQ ID NO:3. Additionally, several hundred separate mutations in the HERG1a polynucleotides (often in the portion shared by HERG1a and HERG1b) known to cause various changes in cardiac $I_{Kr}$ are also known, and additional mutations in HERG1 will undoubtedly be reported. The skilled artisan is in possession of various databases of such mutations (as well as polymorphisms). For example, the Working Group on Arrhythmias of the European Society of Cardiology maintains an online database. Also, the Statens Serum Institute maintains a very similar online database. The current data are provided herein at Table 1, but it will be understood that the skilled artisan can be readily apprised of further cataloged mutations in HERG by consulting the literature or database of such mutations. Additionally, one or a plurality of mutations in either HERG1a, HERG1b, or both, can be incorporated using standard tools of the skilled molecular biologist into one or more of the HERG1 subunits.

It will be understood by the skilled artisan that a line of cultured cells produced according to the invention can comprise in the cell membrane a conventional HERG1b subunit or a mutant HERG1b subunit, optionally in combination with a conventional or mutant HERG1a subunit. It will be appreciated that if the cell line is used in a screening method as described herein, then it is desirable for the cell line to express both the HERG1b and the HERG1a subunits. It is of particular interest to evaluate the potassium ion channel behavior of cell lines carrying conventional HERG1a and HERG1b. Also of significant interest is the potassium ion channel behavior of cell lines carrying conventional HERG1b in combination with HERG1a mutants, even more particularly those HERG1a mutants that differ from conventional HERG1a in the N-terminal portion of the protein not shared with HERG1b. Further, when screening ion channels characteristic of HERG1a-defective mutants, a cell line that comprises HERG1b channels alone is indicated. A HERG1a-defective mutant subunit can be expressed in such cells to simulate channel formation and behavior in native tissue. The skilled artisan will appreciate that mutations in HERG1a- or HERG1b (which can be deletions, insertions, or substitutions) can alter, or can have no effect upon, the activity of the subunits or the channels formed therefrom. The attached list of mutations give a flavor for the types of mutations contemplated, but is not to be considered an exhaustive list.

Any of the aforementioned polynucleotides can be cloned into an expression vector (or plurality of expression vectors) engineered to support expression from the polynucleotides.

Suitable expression vectors comprise a transcriptional promoter active in a recipient cell upstream of the HERG1 polynucleotide and can optionally comprise a polyA-addition sequence downstream of the polynucleotide.

Suitable commercially available expression vectors are pcDNA3.1 and pcDNA3.1zeo (Invitrogen), which differ from one another in that pcDNA3.1 includes sequences conferring resistance to neomycin while pcDNA3.1zeo includes sequences conferring resistance to zeocin. The polyA-addition sequences, not required for expression, can be excised from these vectors by digesting both with ApaI (nuc. 1002) and BbsI (nuc. 1217), respectively, filling in, and self-ligating. The vectors can be prepared to receive the HERG1a or HERG1b polynucleotides, by cleavage with EcoRI and BamHI. For convenience during the subsequent selection step, HERG1a can then be cloned into the cleaved pcDNA3.1 vector; HERG1b can be cloned into the cleaved pcDNA3.1zeo vector. In addition, HERG1a and 1b polynucleotides can be ligated into the two multiple cloning sites of a vector with an internal ribosomal entry site, such as pIRES (Novagen), which allows for production of two separate proteins from a single transcript. Use of this vector to produce clonal cell lines allows for selection with a single antibiotic.

The vector(s) can be introduced (or co-introduced) by, for example, transfection or lipofection, into cells competent to receive and express the HERG1 subunits in their cell membrane. A commercially lipofection kit, such as a kit available for this purpose from Mirus Corporation, Madison, Wis., can be employed. Preferably, the recipient cells do not natively contain HERG1 subunits in their cell membranes, so that the presence of HERG1 channels in the membrane is completely attributable to expression from the introduced expression vector. Suitable recipient cells are human embryonic kidney cells such as cells of the HEK-293 cell line, commercially available from the American Type Culture Collection (Accession Number CRL-1573).

Later, preferably about 24 hours later, cells can be harvested, distributed into wells and grown in selective media. In the exemplified embodiment, a selective medium suitable for selecting cells carrying the HERG1a-vector contains neomycin at 500 micrograms/ml, a medium suited for carrying the HERG1b-vector contains zeocin at 100 micrograms/ml, and a medium suited for growing cells carrying both vectors contains both antibiotics. Cells can be grown under selection for 2-3 weeks until the wells are confluent. Resulting clonal lines (24-48 for each type) can be examined biochemically or electrophysiologically to confirm the presence of the HERG1 channel subunit(s) and the level(s) of HERG produced.

EXAMPLES

Materials and Methods

Cell lines and Antibodies. Human embryonic kidney 293 (HEK-293) cell lines stably expressing conventional HERG1a have been previously described by Zhou, Z., et al., *Biophys J.* 74, 230-241 (1998), and by Furutani, M., et al., *Circulation* 99:2290-2294 (1999), each incorporated by reference as if set forth in its entirety. Cell lines stably expressing HERG1a and HERG1b were prepared by transfecting HEK-293/HERG1a stable cells with HERG1b containing a Kozak consensus sequence cloned into the Bam HI/Eco RI sites of pcDNA3.1zeo (Invitrogen, Carlsbad, Calif.). Separate cell colonies were selected after plating cells at low density and grown in media containing 100 µg/ml Zeocin, 500 µg/ml neomycin for selection. All HEK-293 cells were cultured in Dulbecco's modified Eagle's medium at 37° C.

A polyclonal antibody (termed "ERG-KA") raised against a peptide having an amino acid sequence of CRQRKRKLS-FRRRTDKDTEQ (corresponding to amino acids 883 through 901 of SEQ ID NO:1 plus a non-essential N-terminal cysteine residue provided to permit coupling of the peptide to an immunogenic carrier) can co-precipitate both HERG1a and HERG1b subunits from cardiac myocytes of the HERG channel protein and is diagnostic for the presence of both HERG1a and HERG1b in HERG channels in vivo or in cultured cell lines in vitro. See Roti Roti, E. et al., "Interaction with GM130 during HERG Ion Channel Trafficking," *J. B. C.*, 277:47779 (2002), incorporated herein by reference as if set forth in its entirety. ERG1 isoform-specific antibodies were produced by Bethyl Laboratories (Montgomery, Tex., USA) in rabbits. Antisera were affinity purified using the same peptides employed in immunization. An immunogenic ERG1b peptide was amino acids 12-25 (GALR-PRAQKGRVRR) of SEQ ID NO:4 (HERG1b). The ERG1b antibody was raised against CGALRPRAQKGRVRR, corresponding to the aforementioned amino acids 12-25 plus a non-essential N-terminal cysteine residue provided to permit coupling of the peptide to an immunogenic carrier. An immunogenic ERG1a peptide was amino acids 140-153 (SPAHDT-NHRGPPTS) (Neoclone, Madison, Wis.) of SEQ ID NO:2 (HERG1a). A HERG1a-specific antibody raised in goat (HERG N-20) was purchased from Santa Cruz Biotechnologies (Santa Cruz, Calif.). Horseradish Peroxidase—(HRP-) coupled secondary antibodies were purchased from Pierce (Rockford, Ill.) and Santa Cruz Biotechnology (Santa Cruz, Calif.). Fluorophore-coupled secondary antibodies were purchased from Molecular Probes (Lake Oswego, Oreg.).

Cardiac tissue preparation. Human male ventricular lysate was purchased from ProSci Inc. (Poway, Calif.). Canine ventricular myocytes were isolated from mongrel males and enzymatically treated as described by He, J. Q., et al. (2001), incorporated herein by reference as if set forth in its entirety. Sprague-Dawley rat ventricles were excised from anesthetized adult males after injection of sodium Pentobarbital (100 mg/kg body weight intraperitoneal) as described by He, J. Q, et al. Rat ventricular myocytes were prepared using the same procedure as described for the canine tissue. All procedures were approved by the Research Animal Resources Center (RARC) at UW-Madison.

Cell membrane protein preparations. Membranes were prepared from myocytes or ventricular tissue after suspension in homogenization buffer (in mM: 25 Tris-HCl, pH 7.4; 10 NaEGTA; 20 NaEDTA). All buffers used in this procedure contained the following protease inhibitor cocktail: 5 µg/ml aprotinin, 50 µg/ml 1,10 phenanthroline, 0.7 µg/ml pepstatin A, 1.56 µg/ml benzamidine, and 1× Complete minitab (Roche, Indianapolis, Ind.). Suspensions were homogenized using a Polytron homogenizer at setting 6 for two bursts of 15 seconds each, followed by sonication on ice twice at an amplitude of 20 for 20 seconds each. Suspensions were spun at 2,000×g at 4° C. for 10 minutes to remove cellular debris. The supernatants were subjected to further centrifugation at 40,000×g for 30 minutes at 4° C. The resultant pellet was solubilized on a rotary shaker at 4° C. for 2 hours, in either Triton buffer (in mM: 150 NaCl; 25 Tris-HCl, pH 7.4; 20 NaEDTA; 10 NaEGTA; 5 glucose, and 1% v/v Triton X-100), or RIPA buffer (in mM: 150 NaCl; 50 Tris-HCl, pH 7.4, 1 NaEDTA, and 1% v/v Triton X-100, 1% v/v sodium deoxycholate, 0.1% v/v sodium dodecylsulfate). Samples were then spun at 10,000×g to remove insoluble material. Cell line membrane pellets were prepared by washing plates gently with PBS, aspirating, and adding either Triton buffer or RIPA buffer. Cells were then scraped, collected in a microfuge tube, and sonicated on ice twice at an amplitude of 20 for 20 seconds each. The suspension was rotated at 4° C. for 2 hours and then centrifuged at 10,000×g for 10 minutes to remove insoluble material. Protein concentrations of all samples were determined using a modified Bradford assay (DC Protein Assay, Bio-Rad, Hercules, Calif.).

Biochemical Analysis. Membrane proteins were deglycosylated using PNGase F and Endoglycosidase H (Roche Applied Science, Indianapolis, Ind.) as described by Zhou, Z., et al. (1998), supra, and by Zhou, Z., et al., J Biol Chem 273, 21061-21066 (1998), incorporated herein by reference as if set forth in its entirety. Proteins were denatured at 60° C. to avoid thermal aggregation at higher temperatures. To determine which proteins were expressed on the surface membrane, proteins were surface biotinylated using sulfo-NHS-LC-Biotin reagent. Briefly, 100 mm tissue culture dishes with growth at 70-80% confluency were rinsed three times with cold PBS, and incubated with freshly prepared Biotin reagent (5 mg/ml) in PBS for 45 minutes at 4° C. Cells were then rinsed once with 25 mM Tris-HCl (pH 7.5) to quench the reaction, followed by three washes with cold PBS. Membrane proteins were prepared as indicated above.

Western Blot analysis. Membrane proteins (cell lines 2-10 μg/lane; heart lysates 30-50 μg/lane) were separated on 7.5% SDS-polyacrylamide electrophoresis gels along with prestained molecular weight markers (Bio-Rad, Hercules, Calif.), and were then transferred to PVDF membranes (Immobilon-P, Bedford, Mass.) for 1 hour at 100 mV. Western blots were blocked, probed, and analyzed as described. For peptide block experiments, 5 μl antibody was incubated with 10 μg peptide in 100 μl TBS for 6 hours at 4° C., then centrifuged at 10,000×g for 20 min. The supernatant was carefully removed and used to probe Western blots. Western blot controls include probing blots with secondary antibody alone, and peptide block of primary antibody. In the case of heart lysates, a lane containing HERG1a/1b cell membrane preparation was included as a positive control.

Co-immunoprecipitation. Membrane lysates (cell lines: 100-200 μg/reaction; heart lysates: 500-1000 μg/reaction) in 1 ml TBS (150 mM NaCl, 25 mM Tris-HCl, pH 7.4) were cleared with 50 μl Protein A or G sepharose beads (Amersham, Palatine, Ill.) on immunoprecipitating (IP) antibody; Protein A was used for rabbit and Protein G for goat IP antibodies. Cleared lysates were incubated with antibody (anti-ERG1b at 1/100 or N-20 at 1/20) on a rotating platform for 3-16 hours at 4° C. 50 μl Protein A or G coupled beads were added and samples were incubated at 4° C. for an additional 1-3 h. Beads were collected by centrifugation at 10,000×g, and washed three times with 150 mM NaCl, 25 mM Tris-HCl, pH 7.4, 5 mM NaEDTA, 1% (v/v) Trition X-100, followed by one wash with 150 mM NaCl, 25 mM Tris-HCl, pH 7.4. Proteins were eluted with 200 ng/ml antibody-specific peptide for 1 hour at 4° C. Samples were centrifuged at 10,000×g and the supernatant was collected. 100 μl LSB (25 mM Tris-HCl, pH 6.8, 2% v/v sodium dodecylsulfate, 10% glycerol) was added to the beads to elute any proteins that remained bound. Additional controls included lysates processed without antibody. Eluted proteins were Western blotted as described above.

Immunohistochemistry. Isolated canine myocytes were fixed in 2% paraformaldehyde-PBS, pH 7.4 for 10 minutes at room temperature, and were washed 3× in PBS (pH 7.4). Myocytes were then either stored at 4° C. (for up to 8 weeks) or processed immediately. Myocytes were washed once in PBS (pH 7.4)+1% Triton X-100, and permneabilized in PBS (pH 7.4)+0.5% Triton X-100 for 10 minutes at room temperature followed by incubation in 0.75% glycine-PBS (pH 7.4) for 10 minutes at room temperature to quench any free aldehydes, and incubation in blocking buffer (PBS, pH 7.4,+0.1% Tween-20+10% donkey serum+2% BSA) for 2 hours at 4° C., with rotation. Cells were washed 3× with PBS (pH 7.4)+0.1% Tween-20, and divided into 0.5 ml aliquots. Each myocyte aliquot was incubated overnight at 4° C. in diluted primary antibody. ERG1b antibodies were diluted 1:1000, ERG1a antibodies (N-20), 1:10, and myosin binding protein C antibodies, 1:500. Myocytes were washed 3×1 hour in PBS (pH 7.4)+0.1% Tween-20. Secondary antibodies were diluted in PBS (pH 7.4)+0.1% Tween-20+5% BSA, and spun to remove any aggregates. Myocytes were suspended in 0.5 ml of diluted secondary antibody and incubated in the dark 2 hours at room temperature with rotation. Donkey anti-rabbit Alexa 488 and donkey anti-goat Alexa 568 antibodies were diluted 1:1000. Myocytes were washed briefly 3× with PBS (pH 7.4)+0.1% Tween-20 followed by two 1 hour washes with PBS, pH 7.4 and were stored at 4° C. until viewed on a Zeiss Axiovert 200 with a 63× objective. Optical sectioning was accomplished using the Apotome, and 3D rendering done within Axiovision software. Fluorescent excitation-emission filter set for Alexa 488 (excitation 450-490 nm: emission 515-565 nm) and Alexa 568 (excitation 500-639 nm, emission 560-700 nm) do not overlap. Species specificity of secondary antibodies was confirmed by incubating cells probed with one primary with secondary antibody raised against the other species. No signal was detected demonstrating each secondary is species specific. Secondary alone controls were also used to ensure signal was specific.

Results

On a Western blot of rat heart tissue, the ERG-KA antibody identified three bands at 160, 120, and 95 kD. The two higher molecular mass bands are consistent in size with maturely glycosylated and unglycosylated rat ERG1a, respectively. The 95 kD band is consistent in size with ERG1b protein produced in heterologous expression systems (see below) but had not been previously observed in native tissue. The 95 kD band cannot represent ERG-USO, another HERG1 transcript that produces a protein of approximately the same size, since ERG-USO does not contain the C terminal sequence against which the ERG-KA antibody was raised.

To test the hypothesis that the 95 kD band represents ERG1b, Western blots of membrane proteins prepared from HEK-293 cells stably expressing HERG1a and HERG1b were evaluated with the ERG1a- and ERG1b N termini-specific antibodies. The ERG-KA antibody recognized bands at 155 and 135 kD, consistent with previously published results identifying these bands as mature and immature HERG1 glycoforms, respectively. As expected, blots probed with the ERG1a-specific antibody recognized the 155 and 135 kD bands but not the three lower-mass bands. The 155 and 135 kD bands were eliminated upon incubation of the ERG1a antisera with the antigenic HERG1a peptide prior to probing the blots. Notably, cells expressing HERG1a alone produced only the 155 and 135 kD bands, representing the mature and immature HERG1a species, respectively.

ERG-KA also recognized three lower molecular mass bands at 95, 85 and 80 kD. The ERG1b-specific antibody recognized the 95, 85, and 80 kD bands but not the two higher-mass HERG1a bands. These bands were similarly eliminated by preincubation of the antisera with the antigenic HERG1b peptide. These data show that ERG-KA antisera recognize both HERG1a and HERG1b isoforms, and that ERG1a and HERG1b antisera are specific for their corresponding isoforms.

Membrane proteins from stable HEK-293 HERG1a/1b cell lines were incubated with glycosidases to determine if the multiple HERG1b bands on Western blots correspond to different glycoforms, as shown previously for the HERG1a 155 and 135 kD bands. Removing all glycans from the HERG1b proteins by incubating membrane preparations with PNGase F reduced the higher molecular mass HERG1b species to a single 80 kD band. Digestion with Endoglycosidase H, which removes only glycans that are attached in the ER but not yet processed in the Golgi, reduced the 85 kD band to 80 kD but left the 95 kD band unaltered. Thus, the 95 kD band represents the maturely glycosylated (Golgi-processed) HERG1b isoform, the 85 kD band the core glycosylated, ER-retained form, and the 80 kD band the unglycosylated form. To determine if the mature HERG1b glycoform is expressed on the cell surface, where it could contribute to HERG1 currents, surface proteins were biotinylated prior to cell lysis. Biotinylated proteins were affinity purified with streptavidin beads, Western blotted, and probed with ERG-KA antisera. Like HERG1a, only the maturely glycosylated HERG1b (95 kD) protein band was biotinylated, showing that it is expressed on the cell surface in HEK-293 cells.

In Western blots from two separate human ventricular membrane preparations, the ERG-KA antibody revealed bands at 140, 120, 94 and 83 kD. The 140 and 120 kD bands are consistent with previous reports from human tissue and represent the maturely glycosylated and unglycosylated HERG1a, respectively. The HERG1b-specific antibody recognized the 94 and 83 kD bands, demonstrating that ERG1b protein is expressed in human ventricle.

ERG1b was also observed in Western blots of canine ventricular tissue. There the ERG-KA antibody consistently recognized proteins at 160-165 and 90-95 kD and less consistently at 140-145, 115-125 and 80-85 kD. High molecular weight bands at 165 and 140 kD were recognized by both ERG-KA and ERG1a antibodies and thus represent ERG1a isoforms. The ERG1b antibody recognized the bands at 95 and 83 kD, which were also recognized by ERG-KA, demonstrating that these bands represent ERG1b isoforms. These data show conclusively both ERG1a and ERG1b proteins are expressed within the ventricle across a range of mammalian species.

The antibodies were also characterized by immunocytochemistry using confocal microscopy. The HERG-KA antibody detected HERG1a and HERG1b with a very high sensitivity and little background. The HERG1b-specific antibody stained cells expressing HERG1b but not those expressing HERG1a. The ERG1a antibody gave a high background in immunocytochemistry.

Co-immunoprecipitation Evidence for of HERG1a and HERG1b Heteromerization in Animal Tissue and in HEK-293 Cells Immunoprecipitation studies confirmed that HERG1a and HERG1b co-assemble in heterologous expression systems and in animal tissue. Bidirectional co-immunoprecipitations were carried out in four separate canine cardiac membrane preparations to confirm in vivo assembly. Extracts of fresh, solubilized canine heart tissue were incubated with the HERG1b-specific antibody conjugated to sepharose beads. The beads were concentrated by centrifugation and washed, and the bound proteins were eluted, size-fractionated by SDS-PAGE and transferred to PVDF membrane. At least two membranes were prepared for each eluate. One was probed with the HERG1b-specific antibody to confirm HERG1b immunoprecipitation. The second blot probed with the ERG1a-specific antibody showed HERG1a mature bands, demonstrating HERG1a associates with HERG1b in vivo. The immunoprecipitated proteins were visualized with the HERG-KA antibody, identifying both the precipitating and the associating subunits. The ERG1a-specific antibody immunoprecipitates both mature and immature HERG1a, and co-immunoprecipitates HERG1b. Interestingly, the ERG1a antibody enriched for the mature HERG1b species, relative to its abundance in lysate. Signals were visualized on blots using ECL (Amersham) chemiluminescent detection. The converse IP experiment using bead-bound ERG1a-specific antibody was run to confirm the first IP results. A no-antibody, bead-only control was included in each immunoprecipitation experiment to control for nonspecific precipitation.

Similar results were obtained from one human myocyte preparation immunoprecipitated with the ERG1a specific antibody. These data show that HERG1a and HERG1b proteins associate in mammalian ventricular myocytes in vivo.

To confirm that ERG1a and HERG1b isoforms co-assemble to form heteromeric channels in native tissues, we demonstrated that both ERG1a and ERG1b isoforms are present in rat and canine heart lysates, and that they can be visualized in confocal immunofluorescence microscopy images as puncta along the myocyte sarcolemma, characteristic of a T-tubular distribution. Localization of ERG1a and ERG1b to T-tubular structures in canine ventricular myocytes is consistent with electron microscopy studies in rat myocytes showing ERG1 protein predominantly localized to the T-tubules, where it could regulate action potential duration at the site of excitation-contraction coupling. The signal is similar for both fixed and live cells. No signal was observed when probed only with the secondary antibody. These data suggests that both subunits express at the surface membrane in a similar pattern.

To characterize ERG1 localization more precisely, we stained myocytes concurrently with ERG1a and Myosin binding protein C (MyBP-C) antisera. Three-dimensional images were rendered from a stack of deconvolved two-dimensional immunofluorescent images. MyBP-C signal, in green, appeared as a repeating pattern of doublets separated by regions devoid of fluorescence that span the cell's width. MyBP-C signal localized to the myosin-containing sarcomere A-band; the unstained areas, between doublets, represent M-lines. ERG1a fluorescent signal, shown in red, was seen in I-bands, adjacent to A-bands. Both Z-lines and T-tubules were located in the I-band. The punctate red ERG1a signal extended in columns from the cell surface to the interior, as expected of a T-tubular-restricted protein, where it borders the green MyBP-C signal. These data indicate ERG1 signal in canine myocytes is consistent with a T-tubular distribution.

Co-assembly of HERG1a and HERG1b subunits in stably transfected cell lines.

HERG1a and HERG1b subunits can be co-immunoprecipitated by antibodies specific to either ERG1a or ERG1b subunits from HEK-293 cells. Membrane currents resulting from the co-assembly of these two subunits display characteristic $I_{Kr}$ current profile and sensitivity to E-4031 and anti-arrhythmic drug quinidine.

Figure 2:
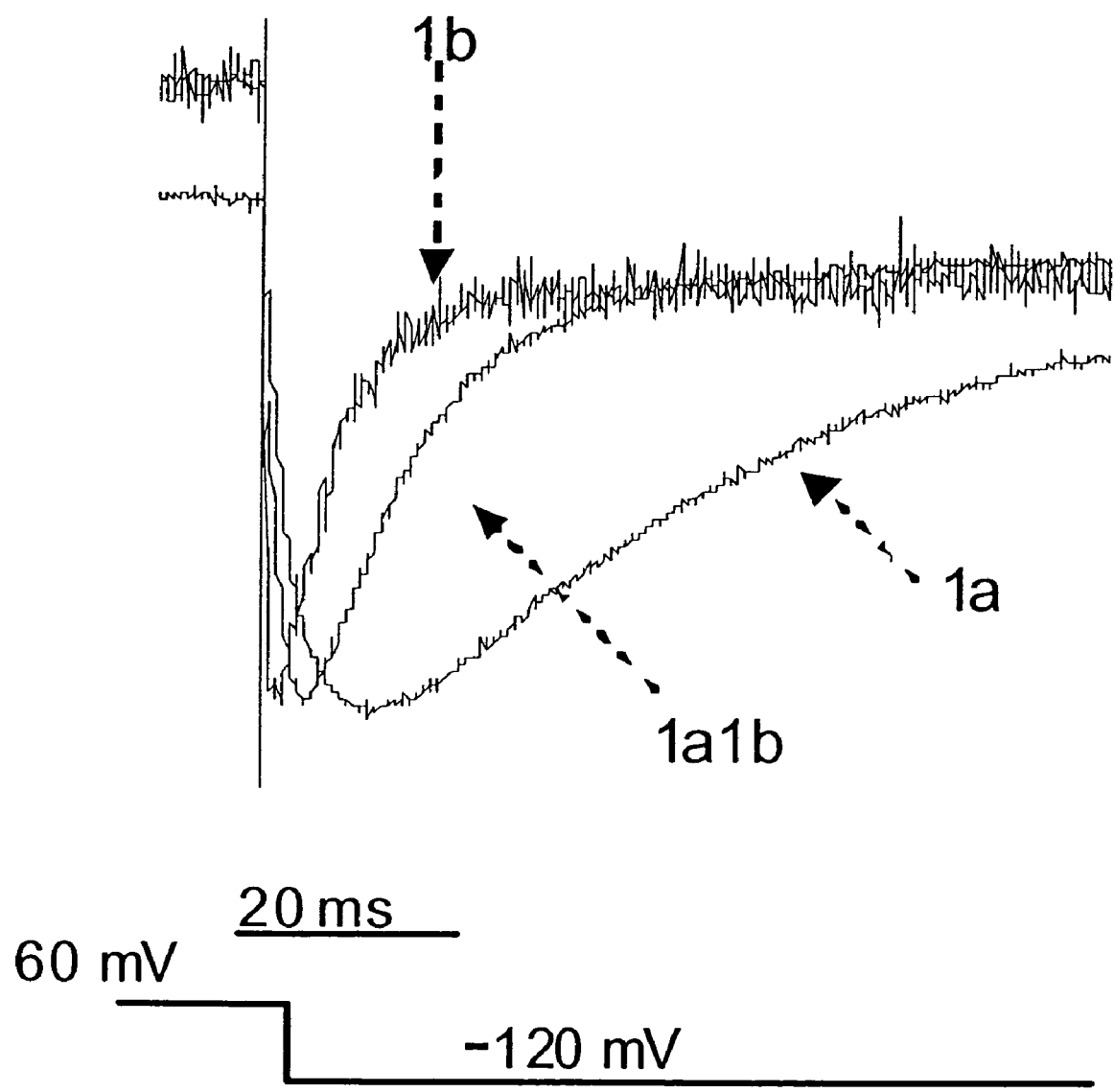
FIG. 2 illustrates an overlay of normalized currents recorded from HEK-293 cells expressing HERG1a, HERG1b and both HERG1a/1b.

FIG. 2 illustrates an overlay of normalized currents recorded from HEK-293 cells expressing HERG1a, HERG1b and both HERG1a/1b. The current of the cells that express HERG1a and HERG1b has the characteristic electrophysiological properties of an $I_{Kr}$ current.

The present invention is not intended to be limited to the foregoing embodiments, but rather to encompass all such modifications and variations as come within the scope of the appended claims.

LITERATURE CITED AND INCORPORATED BY REFERENCE AS IF SET FORTH HEREIN IN ITS ENTIRETY

Abbott, G W, Sesti F, Splawski I, Buck M E, Lehmann M H, Timothy K W, Keating M T, Goldstein S A (1999) MiRP1 forms IKr potassium channels with HERG and is associated with cardiac arrhythmia. Cell 97:175-187.

Brette, F., and Orchard, C. (2003) Circ Res 92, 1182-1192

Chen, J., Zou, A., Splawski, I., Keating, M. T., and Sanguinetti, M. C. (1999) J Biol Chem 274, 10113-10118

Christie, M J, North R A, Osborne P B, Douglass J, Adelman J P (1990) Heteropolymeric potassium channels expressed in Xenopus oocytes from cloned subunits. Neuron 4:405-411.

Craig, R., and Offer, G. (1976) Proc R Soc Lond B Biol Sci 192, 451-461

Crociani, O, Guasti L, Balzi M, Becchetti A, Wanke E, Olivotto M, Wymore R S, Arcangeli A (2003) Cell cycle-dependent expression of HERG1 and HERG1B isoforms in tumor cells. J. Biol. Chem. 278: 2947-2955.

Cui, J, Melman Y, Palma E, Fishman G I, McDonald T V (2000) Cyclic AMP regulates the HERG K(+) channel by dual pathways. Curr Biol 10:671-674.

Curran, M E, Splawski I, Timothy K W, Vincent G M, Green E D, Keating M T (1995) A molecular basis for cardiac arrhythmia: HERG mutations cause long QT syndrome. Cell 80:795-803.

Delisle, B. P., Anderson, C. L., Balijepalli, R. C., Anson, B. D., Kamp, T. J., and January, C. T. (2003) J Biol Chem 278, 35749-35754

Deutsch, C (2002) Potassium channel ontogeny. Annu Rev Physiol 64:19-46.

Ellgaard, L, Helenius A (2003) Quality control in the endoplasmic reticulum. Nat Rev Mol Cell Biol 4:181-191.

England, S K, Uebele V N, Shear H, Kodali J, Bennett P B, Tamkun M M (1995) Characterization of a voltage-gated K+ channel beta subunit expressed in human heart. Proc Natl Acad Sci U S A 92:6309-6313.

Ficker, E K, Thomas D, Viswanathan P, Rudy Y, Brown A M (2000) Rescue of a misprocessed mutant HERG channel linked to hereditary long QT syndrome. Biophysical Journal 78:342A.

Finley, M. R., Li, Y., Hua, F., Lillich, J., Mitchell, K. E., Ganta, S., Gilmour, R. F., and Freeman, L. C. (2002) Am J Physiol 283, H126-H138

Gossen, M, Freundlieb S, Bender G, Muller G, Hillen W, Bujard H (1995) Transcriptional activation by tetracyclines in mammalian cells. Science 268:1766-1769.

Gulbis, J M, Zhou M, Mann S, MacKinnon R (2000) Structure of the cytoplasmic beta subunit-T1 assembly of voltage-dependent K+ channels. Science 289:123-127.

Guo, W, Li H, Aimond F, Johns D C, Rhodes K J, Trimmer J S, Nerbonne J M (2002) Role of heteromultimers in the generation of myocardial transient outward K+ currents. Circ Res 90:586-593.

Harris, S. P., Bartley, C. R., Hacker, T. A., McDonald, K. S., Douglas, P. S., Greaser, M. L., Powers, P. A., and Moss, R. L. (2002) Circ Res 90, 594-601

He, J. Q., Conklin, M. W., Foell, J. D., Wolff, M. R., Haworth, R. A., Coronado, R., and Kamp, T. J. (2001) Cardiovascular Research 49, 298-307

Huxley, A. F., and Niedergerke, R. (1954) Nature 173, 971-973

Isacoff, E Y, Jan Y N, Jan L Y (1990) Evidence for the formation of heteromultimeric potassium channels in Xenopus oocytes. Nature 345:530-534.

Ishii, M, Kurachi Y (2002) The 14-3-3 protein as a novel regulator of ion channel localisation. J Physiol 545:2.

Kagan, A, Melman Y F, Krumerman A, McDonald T V (2002) 14-3-3 amplifies and prolongs adrenergic stimulation of HERG K+ channel activity. EMBO J 21:1889-1898.

Kosolapov, A, Deutsch C (2003) Folding of the voltage-gated K+ channel T1 recognition domain. J Biol Chem 278: 4305-4313.

Kupershmidt, S, Snyders D J, Raes A, Roden D M (1998) A K+ channel splice variant common in human heart lacks a C-terminal domain required for expression of rapidly activating delayed rectifier current. J Biol Chem 273:27231-27235.

Lees-Miller, J P, Kondo C, Wang L, Duff H J (1997) Electrophysiological characterization of an alternatively processed ERG K+ channel in mouse and human hearts. Circ Res 81:719-726.

Lees-Miller, J P, Guo J, Somers J R, Roach D E, Sheldon R S, Rancourt D E, Duff H J (2003) Selective knockout of mouse ERG1 B potassium channel eliminates I(Kr) in adult ventricular myocytes and elicits episodes of abrupt sinus bradycardia. Mol Cell Biol 23:1856-1862.

Li, M, Jan Y N, Jan L Y (1992) Specification of subunit assembly by the hydrophilic amino-terminal domain of the Shaker potassium channel. Science 257:1225-1230.

Li, X, Xu J, Li M (1997) The human delta1261 mutation of the HERG potassium channel results in a truncated protein that contains a subunit interaction domain and decreases the channel expression. J Biol Chem 272:705-708.

London, B, Aydar E, Lewarchik C, Seibel J S, January C T, Robertson G A (1998) N and C-terminal isoforms of HERG in the human heart. Biophysical J.

London, B, Trudeau M C, Newton K P, Beyer A K, Copeland N G, Gilbert D J, Jenkins N A, Satler C A, Robertson G A (1997) Two isoforms of the mouse ether-a-go-go-related gene co-assemble to form channels with properties similar to the rapidly activating component of the cardiac delayed rectifier K+ current. Circ Res 81:870-878.

Lu, J, Robinson J M, Edwards D, Deutsch C (2001) T1-T1 interactions occur in ER membranes while nascent Kv peptides are still attached to ribosomes. Biochemistry 40:10934-10946.

Larsen, L. A., Andersen, P. S., Kanters, J., Svendsen, I. H., Jacobsen, J. R., Vuust, J., Wettrell, G., Tranebjaerg, L., Bathen, J., and Christiansen, M. (2001) Clinical Chemistry 47, 1390-1395

MacKinnon, R (1991) Determination of the subunit stoichiometry of a voltage-activated potassium channel. Nature 350:232-235.

Mohammad, S, Zhou Z, Gong Q, January C T (1997) Blockage of the HERG human cardiac K+ channel by the gastrointestinal prokinetic agent cisapride. Am J Physiol 273: H2534-2538.

Morais, Cabral J H, Lee A, Cohen S L, Chait B T, Li M, Mackinnon R (1998) Crystal structure and functional analysis of the HERG potassium channel N terminus: a eukaryotic PAS domain. Cell 95:649-655.

Newitt, R A, Houamed K M, Rehm H, Tempel B L (1991) Potassium channels and epilepsy: evidence that the epileptogenic toxin, dendrotoxin, binds to potassium channel proteins. Epilepsy Res Suppl 4:263-273.

O'Kelly, I, Butler M H, Zilberberg N, Goldstein S A (2002) Forward transport. 14-3-3 binding overcomes retention in endoplasmic reticulum by dibasic signals. Cell 111:577-588.

Papazian, D M, Shao X M, Seoh S A, Mock A F, Huang Y, Wainstock D H (1995) Electrostatic interactions of S4 voltage sensor in Shaker K+ channel. Neuron 14:1293-1301.

Paulussen, A., Raes, A., Matthijs, G., Snyders, D. J., Cohen, N., and Aerssens, J. (2002) *J Biol Chem* 277, 48610-48616

Petcherski, A G, Kimble J (2000) LAG-3 is a putative transcriptional activator in the C. elegans Notch pathway. Nature 405:364-368.

Pond, A L, Scheve B K, Benedict A T, Petrecca K, Van Wagoner D R, Shrier A, Nerbonne J M (2000) Expression of distinct ERG proteins in rat, mouse, and human heart. Relation to functional I(Kr) channels. J Biol Chem 275: 5997-6006.

Rampe, D, Roy M L, Dennis A, Brown A M (1997) A mechanism for the proarrhythmic effects of cisapride (Propulsid): high affinity blockade of the human cardiac potassium channel HERG. FEBS Lett 417:28-32.

Rasmussen, H. B., Moller, M., Knaus, H. G., Jensen, B. S., Olesen, S. P., and Jorgensen, N. K. (2004) *Am J Physiol* 286, H1300-H1309

Robertson, G A (2000) LQT2: amplitude reduction and loss of selectivity in the tail that wags the HERG channel [editorial; comment]. Circ Res 86:492-493.

Roden, D M (1993) Torsade de pointes. Clin Cardiol 16:683-686.

Roti Roti, E C, Myers C D, Ayers R A, Boatman D E, Delfosse S A, Chan E K, Ackerman M J, January C T, Robertson G A (2002) Interaction with GM130 during HERG ion channel trafficking. Disruption by type 2 congenital long QT syndrome mutations. Human Ether-a-go-go-Related Gene. J Biol Chem 277:47779-47785.

Roy, M, Dumaine R, Brown A M (1996) HERG, a primary human ventricular target of the nonsedating antihistamine terfenadine [see comments]. Circulation 94:817-823.

Sanguinetti, M C, Jurkiewicz N K (1990) Two components of cardiac delayed rectifier K+ current. Differential sensitivity to block by class III antiarrhythmic agents. J Gen Physiol 96:195-215.

Sanguinetti, M C, Jiang C, Curran M E, Keating M T (1995) A mechanistic link between an inherited and an acquired cardiac arrhythmia: HERG encodes the IKr potassium channel. Cell 81:299-307.

Sanguinetti, M C, Curran M E, Zou A, Shen J, Spector P S, Atkinson D L, Keating M T (1996), Co-assembly of K(V) LQT1 and minK (IsK) proteins to form cardiac I(Ks) potassium channel. Nature 384:80-83.

Shen, N V, Pfaffinger P J (1995) Molecular recognition and assembly sequences involved in the subfamily-specific assembly of voltage-gated K+ channel subunit proteins. Neuron 14:625-633.

Shi, W, Wymore R S, Wang H S, Pan Z, Cohen I S, McKinnon D, Dixon J E (1997) Identification of two nervous system-specific members of the erg potassium channel gene family. J Neurosci 17:9423-9432.

Snyders, D J, Chaudhary A (1996) High affinity open channel block by dofetilide of HERG expressed in a human cell line. Mol Pharmacol 49:949-955.

Splawski, I, Tristani-Firouzi M, Lehmann M H, Sanguinetti M C, Keating M T (1997) Mutations in the hminK gene cause long QT syndrome and suppress IKs function. Nat Genet 17:338-340.

Suessbrich, H, Waldegger S, Lang F, Busch A E (1996) Blockade of HERG channels expressed in *Xenopus* oocytes by the histamine receptor antagonists terfenadine and astemizole. FEBS Lett 385:77-80.

Thomas, D, Zhang W, Karle C A, Kathofer S, Schols W, Kubler W, Kiehn J (1999) Deletion of protein kinase A phosphorylation sites in the HERG potassium channel inhibits activation shift by protein kinase A. J Biol Chem 274:27457-27462.

Trudeau, M C, Warmke J W, Ganetzky B, Robertson G A (1995) HERG, a human inward rectifier in the voltage-gated potassium channel family. Science 269:92-95.

Tu, L, Deutsch C (1999) Evidence for dimerization of dimers in K+ channel assembly. Biophys J 76:2004-2017.

Wang, J, Myers C D, Robertson G A (2000) Dynamic control of deactivation gating by a soluble amino-terminal domain in HERG K(+) channels. J Gen Physiol 115:749-758.

Warmke, J W, Ganetzky B (1994) A family of potassium channel genes related to eag in Drosophila and mammals. Proc Natl Acad Sci U S A 91:3438-3442.

Xu, J, Yu W, Jan Y N, Jan L Y, Li M (1995) Assembly of voltage-gated potassium channels. Conserved hydrophilic motifs determine subfamily-specific interactions between the alpha-subunits. J Biol Chem 270:24761-24768.

Yang, T., Wathen, M. S., Felipe, A., Tamkun, M. M., Snyders, D. J., and Roden, D. M. (1994) *Circ Res* 75, 870-878

Yuan, H, Michelsen K, Schwappach B (2003) 14-3-3 dimers probe the assembly status of multimeric membrane proteins. Curr Biol 13:638-646.

Zerangue, N, Schwappach B, Jan Y N, Jan L Y (1999) A new ER trafficking signal regulates the subunit stoichiometry of plasma membrane K(ATP) channels. Neuron 22:537-548.

Zhou, Z, Gong Q, January C T (1999a) Correction of defective protein trafficking of a mutant HERG potassium channel in human long QT syndrome. Pharmacological and temperature effects. J Biol Chem 274:31123-31126.

Zhou, Z, Gong Q, Epstein M L, January C T (1998a) HERG channel dysfunction in human long QT syndrome. Intracellular transport and functional defects. J Biol Chem 273: 21061-21066.

Zhou, Z, Vorperian V R, Gong Q, Zhang S, January C T (1999b) Block of HERG potassium channels by the antihistamine astemizole and its metabolites desmethylastemizole and norastemizole. J Cardiovasc Electrophysiol 10:836-843.

Zhou, Z, Gong Q, Ye B, Fan Z, Makielski J C, Robertson G A, January C T (1998b) Properties of HERG channels stably expressed in HEK 293 cells studied at physiological temperature. Biophys J 74:230-241.

TABLE 1

KCNH2 (HERG) mutations

| Nucleotide change | Mutation | Coding effect | Region | Ethnic background | Reference | More data |
|---|---|---|---|---|---|---|
| — | S26I | Missense | PAS domain | USA | Moss et al, 2002 | |
| 87C > A | F29L | Missense | PAS domain | USA | Chen et al, 1999, Splawski et al, 2000 | |

TABLE 1-continued

KCNH2 (HERG) mutations

| Nucleotide change | Mutation | Coding effect | Region | Ethnic background | Reference | More data |
|---|---|---|---|---|---|---|
| 98A > C | N33T | Missense | PAS domain | USA | Chen et al, 1999, Splawski et al, 2000 | |
| 132C > A | C44X | Missense | PAS domain | USA | Splawski et al, 2000 | |
| 140G > T | G47V | Missense | PAS domain | USA | Splawski et al, 2000 | |
| 157G > C | G53R | Missense | PAS domain | USA | Chen et al, 1999, Splawski et al, 2000 | |
| 167G > A | R56Q | Missense | PAS domain | USA | Chen et al, 1999, Splawski et al, 2000 | |
| 196T > G | C66G | Missense | PAS domain | USA | Chen et al, 1999, Splawski et al, 2000 | |
| 209A > G | H70R | Missense | PAS domain | USA | Chen et al, 1999, Splawski et al, 2000 | |
| 215C > A | P72Q | Missense | PAS domain | USA | Splawski et al, 2000 | |
| 221–251del | 31 bp deletion | Frameshift | PAS domain | USA | Splawski et al, 2000 | |
| 234–250dup | 16 bp duplication | Frameshift | PAS domain | USA | Splawski et al, 2000 | |
| — | A78P | Missense | PAS domain | USA | Moss et al, 2002 | |
| 241C > T | Q81X | Nonsense | Pas domain | USA | Splawski et al, 2000 | |
| 244–252 ins9 | 82–84insIAQ | Duplication | PAS-domain | Da | Larsen et al, 2001 | |
| — | fs83/37aa | Frameshift | PAS domain | USA | Moss et al, 2002 | |
| 257G > T | L86R | Missense | PAS domain | USA | Chen et al, 1999, Splawski et al, 2000 | |
| 260T > C | L87P | Missense | PAS domain | Du | Jongbloed et al, 2002 | |
| 287T > C | I96T | Missense | PAS-domain | Da | Larsen et al, 2001 | |
| 296A > C | Y99S | Missense | PAS domain | Du | Jongbloed et al, 2002 | |
| 391A > G | K101E | Missense | PAS-domain | Da | Larsen et al, 2001 | |
| — | M124R | Missense | — | USA | Moss et al, 2002 | |
| 422insC | 1 bp insertion | Frameshift | PAS-S1 | USA | Splawski et al, 2000 | |
| 453insC | 1 bp insertion | Frameshift | PAS-S1 | USA | Splawski et al, 2000 | |
| 453delC | 1 bp deletion | Frameshift | PAS-S1 | Fi | Swan et al, 1999, Lätinen et al, 2000 | |
| 526C > T | R176W | Missense | PAS-S1 | Fi | Swan et al, 1999, Lätinen et al, 2000 | |
| 558–600dup | 42 bp duplication | Frameshift | PAS-S1 | Mediteranean | Hoorntje et al, 1999 | |
| 582–587 delCCGTG | G192fs328 | Deletion | PAS-S1 | Du | Jongbloed et al, 2002 | |
| 724insC | 1 bp insertion | Frameshift | PAS-S1 | USA | Splawski et al, 2000 | |
| 885delC | 1 bp insertion | Frameshift | PAS-S1 | USA | Splawski et al, 2000 | |
| — | FsV295/63aa | Frameshift | PAS-S1 | USA | Moss et al, 2002 | |
| 934C > T | R312C | Missense | PAS-S1 | USA | Splawski et al, 2000 | |
| 1039G > A | P347S | Missense | PAS-S1 | USA | Splawski et al, 2000 | |
| 1039C > T | P347S | Missense | PAS-S1 | Du | Jongbloed et al, 2002 | |
| 1096C > T | R366X | Nonsense | PAS-S1 | Da | Larsen et al, 2001 | |
| — | Q376- | Splice site | PAS-S1 | USa | Moss et al, 2002 | |
| 1128G > A | — | Splice site | PAS-S1 | USA | Splawski et al, 2000 | |
| 1129-2 G > A | — | Splice site | PAS-S1 | USA | Splawski et al, 2000 | |
| 1199T > A | I100N | Missense | S1 | Da | Larsen et al, 2001 | |
| 1261delA | 1 bp deletion | Frameshift | S1 | It | Curran et al, 1995 | |
| 1283C > A | S428X | Nonsense | S1-S2 | It | Priori et al, 1999 | |
| — | S428L | Missense | S1-S2 | USA | Moss et al, 2002 | |
| 1307C > T | T436M | Missense | S1-S2 | It | Priori et al, 1999 | |
| 1341C > A | Y447X | Nonsense | S1-S2 | Du | Jongbloed et al, 2002 | |
| 1352C > T | P451L | Missense | S2 | Fi | Lätinen et al, 2000 | |
| 1408A > G | N470D | Missense | S2 | Me, Ge, Eng, Da | Curran et al, 1995 | |
| 1421C > T | T474I | Missense | S2-S3 | Ja | Tanaka et al, 1997 | |
| 1479C > G | Y493X | Nonsense | S2-S3 | Ja | Itoh et al, 1998 | |
| 1496–1523dle | I500-F508del | Deletion | S3 | Me, Ge, Eng, Da | Curran et al, 1995 | |
| 1501A > G | D501N | Missense | S3 | Du | Jongbloed et al, 2002 | |

TABLE 1-continued

KCNH2 (HERG) mutations

| Nucleotide change | Mutation | Coding effect | Region | Ethnic background | Reference | More data |
|---|---|---|---|---|---|---|
| 1592G > A | R531Q | Missense | S3 | USA | Splawski et al, 2000 | |
| — | L552S | Missense | S3 | USA | Moss et al, 2002 | |
| 1600C > T | R635C | Missense | S4 | Ja | Itoh et al, 1998, Nakajima et al, 1999 | |
| 1631delAG | 2 bp deletion | frameshift | S4-S5 | Fi | Wsan et al, 1999, Lätinen et al, 2000 | |
| 1655T > C | L552S | Missense | S5 | Fi, USA | Swan et al, 1999, Splawski et al, 2000 | |
| 1672G > C | A558P | Missense | S5 | Du | Jongbloed et al, 1999 | |
| 1681G > A | A561T | Misense | S5 | Fr, USA | Dausse et al, 1996, Splawski et al, 2000 | |
| 1682C > T | A561V | Missense | S5 | Me, Ge, Emg, Da, Ja, USA | Curran et al, 1995, Tanaka et al, 1997, Priori et al, 1999, Larsen et al, unpublished, Splawski et al, 2000 | |
| 1691T > C | L564P | Missense | S5 | Fr, Ca | St-Pierre et al, 2000 | |
| 1705T > C | Y569H | Missense | S5 | Fi | Swan et al, 1999, Lätinen et al, 2000 | |
| 1714G > C | G572R | Missense | S5-pore | Da | Larsen et al, 2000 | |
| 1714G > T | G572C | Missense | S5-pore | Du | Jongbloed et al, 1999 | |
| 1750G > A | W585C | Missense | S5-pore | Fi, USA | swan et al, 1999, Splawski et al, 2000, Lätinen et al, 2000 | |
| 1755G > T | W585C | Missense | S5-pore | USA | Splawski et al, 2000 | |
| 1762A > G | N588D | Missense | S5-pore | USA | Splawski et al, 2000 | |
| 1778T > C | I593B | Missense | S5-pore | Eng?, USA | Benson et al, 1996, Splawski et al, 2000 | |
| 1778T > G | I593G | Missense | S5-pore | USA | Benson et al, 1996, Splawski et al, 2000 | |
| — | I593X | Nonsense | S5-pore | USA | Moss et al, 2002 | |
| — | P596L | Missense | S5-pore | USA | Moss et al, 2002 | |
| 1801G > A | G601S | Missense | S5-pore | Ja, Fi | Akimoto et al, 1997, Swan et al, 1999, Lätinen et al, 2000 | |
| 1810G > A | G604S | Missense | S5-pore | Du, USA | Jongbloed et al, 1999, Splawski et al, 2000 | |
| 1825G > A | D609N | Missense | S5-pore | USA | Splawski et al, 2000 | |
| 1831T > C | Y611H | Missense | S5-pore | Ja | Tanaka et al, 1997 | |
| 1833T > A/G | Y611X | Nonsense | S5-pore | Ge | Schultze-Bahr et al, 1995 | |
| 1834G > T | V612L | Missense | S5-pore | Ir, It, Du | Satler et al, 1998 | |
| 1838C > T | T613M | Missense | S5-Pore | Du, Fi | Jongbloed et al, 1999, Lätinen et al, 2000 | |
| 1842C > T | A614V | Missense | Pore | Ja, Ir, Cz, Eng, Fr, Fi, It, Tw | Tanaka et al, 1997, Satler et al, 1998, Splawski er al, 1998, Priori et al, 1999, Lee-Chen et al, 1999 | |
| 1843G > | L615V | Missense | Pore | USA | Splawski et al, 2000 | |
| 1862G > A | S621N | Missense | Pore | Da | Larsen et al, 2001 | |
| 1876G > A | G626S | Missense | Pore | USA | Splawski et al, 2000 | |
| 1877G > T | G626V | Missense | pore | Ge | Jahr et al, 2000 | |
| 1881G > C | F627L | Missense | Pore | USA | splawski et al, 2000 | |
| 1882G > A | G628S | Missense | Pore | Me, Ge, Eng, Da | Curran et al, 1995, Splawski et al, 2000 | |
| 1885A > G | N629D | Missense | Pore | Ge, Ir, Na | Satler et al, 1998, Lees-Miller et al, 2000 | |
| 1886A > G | N629S | Missense | Pore | Unknown, Da | Satler et al, 1998, Larsen et al, unpublished | |
| — | N629K | Missense | Pore | Ja | Yoshida et al, 1999 | |
| 1888G > C | V630L | Missense | Pore | Ja | Tanaka et al, 1997 | |
| 1889T > C | V630A | Missense | Pore | USA | Splawski et al, 1998 | |
| 1894C > T | P632S | Missense | Pore | USA | Splawski et al, 2000 | |
| 1898A > G | N633S | Missense | Pore | Eng | Satler et al, 1998 | |
| 1912A > G | K638E | Missense | S6 | USA | Splawski et al, 2000 | |
| 1913-15del | K638del | Deletion | S6 | USA | Splawski et al, 2000 | |
| 1920C > A | F640L | Missense | S6 | Du | Jongbloed et al, 1999 | |
| 1933A > T | M645L | Missense | S6 | USA | Splawski et al, 2000 | |
| 1951–1952 delAT | 2 bp deletion | Frameshift | S6 | Ja | Itoh et al, 1998 | |
| 2001C > A | Y667X | Nonsense | S6 | Be | Paulussen et al, 2000 | |
| 2044G > T | E682X | Nonsense | S6 | USA | Splawski et al, 2000 | |
| 2092G > T | E698X | Nonsense | S6 | Du | Jongbloed et al, 2002 | |
| 2173C > T | Q725X | Nonsense | S6 | Ja | Itoh et al, 1998 | |
| 2218insT | 1 bp insertion | Frameshift | S6-- | USA | Splawski et al, 2000 | |
| 2232C > T | R744X | Nonsense | S6-- | Tw | Ko et al, 2001 | |
| 2254C > T | R752W | Nonsense | S6-- | USA | Splawski et al, 2000, Ficher e al, 2000 | |
| 2350C > T | R784W | Missense | S6-- | USA | Yang et al, 2002 | |

TABLE 1-continued

KCNH2 (HERG) mutations

| Nucleotide change | Mutation | Coding effect | Region | Ethnic background | Reference | More data |
|---|---|---|---|---|---|---|
| 2356–2376 dup | 31 bp duplication | Frameshift | CNB domain | Ja | Itoh et al, 1998 | |
| 2395delC | 1 bp deletion | Frameshift | CNB domain | USA | Splawski et al, 2000 | |
| 2398 + 1G > C | IVS9 DS + 1 | Splice mutation | CNB domain | USA | Curran et al, 1995 | |
| 2414T > C | F805S | Missense | CNB domain | USA | Splawski et al, 2000 | |
| 2414T > G | F805C | Missense | CNB domain | USA | Splawski et al, 2000 | |
| 2453C > T | S818L | Missense | CNB domain | Fr | Berthet et al, 1999 | |
| 2464G > A | V822M | Missense | CNB domain | Ir, Fr | Satler et al, 1996, Berthet et al, | |
| 2467C > T | R823W | Missense | CNB domain | USA | Spalwski et al, 2000 | |
| 2471insG | R823fs828 | Deletion | CNB domain | Du | Jongbloed et al, 2000 | |
| 2582A > T | N861I | Missense | C-terminal | USA | Splawski et al, 2000 | |
| 2592 + 1G > A | IVS1 + DS + 1 | Frameshift | C-terminal | Be, USA | Berthet et al, 1999 Splawski et al, 2000 | |
| 2616delC | P872fs877 | Deletion | C-terminal | Du | Jongbloed et al, 2002 | |
| 2660delG | 1 bp deletion | Frameshift | C-termnal | USA | Splawski et al, 2000 | |
| 2750C > T | R917L | Missense | C-terminal | USA | Splawski et al, 2000 | |
| 2762delA | 1bP deletion | Frameshift | C-terminal | USA | Splawski et al, 2000 | |
| 2764C > T | R922W | Missense | C-terminal | USA | Splawski et al, 2000 | |
| 2775insG | 1 bp insertion | Frameshift | C-terminal | USA | Splawski et al, 2000 | |
| 2906delG | 1 bp deletion | Frameshift | C-terminal | USA | Splawski et al, 2000 | |
| — | P968/4aa | Frameshift | C-terminal | USA | Moss et al, 2002 | |
| 2959delCT | 2 bp deletion | Frameshift | C-terminal | USA | Splawski et al, 2000 | |
| — | W1001X | Nonsense | C-terminal | USA | Moss et al, 2002 | |
| 3040C > T | R1014X | Nonsense | C-terminal | USA | Splawski et al, 2000 | |
| 3094delC | 1 bp deletion | Frameshift | C-terminal | USA | Splawski et al, 2000 | |
| 3108insG | — | Frameshift | C-terminal | Sp | Berthet et al, 1999 | |
| 3303insC | 1 bp insertion | Frameshift | C-terminal | USA | Splawski et al, 2000 | |
| Aminoacid polymorphisms | | | | | | |
| 2690A > C | K897T | — | — | — | Iwasa et al, 2000, Lätinen et al, 2000, Yang et al, 2002 | |
| — | R1047L | — | — | — | Larsen et al, 2001 | |
| Single nucleotide polymorphisms (SNPs) | | | | | | |
| IVS2 + 27G > C | Intron variant | SNP | — | — | Jongbloed et al, 2002 | |
| IVS8-61 A/G | Intron variant | SNP | — | — | Larsen et al, 2001 | |
| IVS13 + 12 C/A | Intron variant | SNP | — | — | Larsen et al, 2001 | |
| IVS13 + 22 A/G | Intron variant | SNP | — | — | Larsen et al, 2001 | |
| 1467C > T | I489I | SNP | — | — | Akimoto et al, 1997 | |
| 1539C > T | F513F | SNP | — | — | Akimoto et al, 1997 | |
| 1692A > G | L564L | SNP | — | — | Akimoto et al, 1997 | |
| 1956T > C | Y652Y | SNP | — | — | Larsen et al, 1999 | |
| 2965 + 22 A > G | Intronic variant | — | — | — | Iwasa et al, 2000 | |

[1] Ja: Japanese, Ir: Irish, Cz: Czech, Eng: English., Ge: German, Fr: French, Fil: Filipino, Fi: Finnish, Na: Native american, Me. Mexican, Da: Danish, It: Italian, Du: Dutch, Sp: Spanish. Be: Belgian.Tw: Taiwanese.
[2] Region distal to S6.

We claim:

1. A cultured mammalian cell line characterized in that cells in the line express an HERG1b subunit component comprising SEQ ID NO:4, wherein the cell line does not natively express the HERG1b subunit.

2. A cultured cell line as claimed in claim 1 further comprising an HERG1a subunit component comprising SEQ ID NO:2.

3. A cultured cell line as claimed in claim 1 wherein cells in the line comprise SEQ ID NO:3 from nucleotide 325 to nucleotide 2784.

4. A cultured cell line as claimed in claim 3 wherein the cell line further comprises SEQ ID NO:1 from nucleotide 14 to nucleotide 3493.

5. A cultured mammalian cell line that produces a membrane current, wherein cells in the line comprising a first heterologous polynucleotide that encodes HERG1a and a second heterologous polynucleotide that encodes HERG1b, the current being characterized as exhibiting rapid inactivation, slow deactivation under a step voltage protocol and sensitivity to a methanesulfonanilide drug, wherein the first polynucleotide comprises SEQ ID NO:1 from nucleotide 14 to nucleotide 3493, and wherein the second polynucleotide comprises SEQ ID NO:3 from nucleotide 325 to nucleotide 2784, and wherein the cell line does not natively express the first and second heterologous polynucleotides.

6. A cultured cell line as claimed in claim 5 wherein the cell line is a human cell line.

7. A cultured cell line as claimed in claim 6 wherein the human cell line is HEK-293 stably transformed with the first and second polynucleotides.

\* \* \* \* \*

SEQUENCE LISTING

<160> NUMBER OF SEQ ID NOS: 4

<210> SEQ ID NO 1
<211> LENGTH: 3900
<212> TYPE: DNA
<213> ORGANISM: Homo sapiens
<220> FEATURE:
<221> NAME/KEY: CDS
<222> LOCATION: (14)..(3493)

<400> SEQUENCE: 1

```
ccatgggctc agg atg ccg gtg cgg agg ggc cac gtc gcg ccg cag aac           49
            Met Pro Val Arg Arg Gly His Val Ala Pro Gln Asn
              1               5                  10 acc ttc ctg gac acc atc atc cgc aag ttt gag ggc cag agc cgt aag          97
Thr Phe Leu Asp Thr Ile Ile Arg Lys Phe Glu Gly Gln Ser Arg Lys
         15                  20                  25 ttc atc atc gcc aac gct cgg gtg gag aac tgc gcc gtc atc tac tgc         145
Phe Ile Ile Ala Asn Ala Arg Val Glu Asn Cys Ala Val Ile Tyr Cys
     30                  35                  40 aac gac ggc ttc tgc gag ctg tgc ggc tac tcg cgg gcc gag gtg atg         193
Asn Asp Gly Phe Cys Glu Leu Cys Gly Tyr Ser Arg Ala Glu Val Met
 45                  50                  55                  60 cag cga ccc tgc acc tgc gac ttc ctg cac ggg ccg cgc acg cag cgc         241
Gln Arg Pro Cys Thr Cys Asp Phe Leu His Gly Pro Arg Thr Gln Arg
                 65                  70                  75 cgc gct gcc gcg cag atc gcg cag gca ctg ctg ggc gcc gag gag cgc         289
Arg Ala Ala Ala Gln Ile Ala Gln Ala Leu Leu Gly Ala Glu Glu Arg
             80                  85                  90 aaa gtg gaa atc gcc ttc tac cgg aaa gat ggg agc tgc ttc cta tgt         337
Lys Val Glu Ile Ala Phe Tyr Arg Lys Asp Gly Ser Cys Phe Leu Cys
         95                 100                 105 ctg gtg gat gtg gtg ccc gtg aag aac gag gat ggg gct gtc atc atg         385
Leu Val Asp Val Val Pro Val Lys Asn Glu Asp Gly Ala Val Ile Met
    110                 115                 120 ttc atc ctc aat ttc gag gtg gtg atg gag aag gac atg gtg ggg tcc         433
Phe Ile Leu Asn Phe Glu Val Val Met Glu Lys Asp Met Val Gly Ser
125                 130                 135                 140 ccg gct cat gac acc aac cac cgg ggc ccc ccc acc agc tgg ctg gcc         481
Pro Ala His Asp Thr Asn His Arg Gly Pro Pro Thr Ser Trp Leu Ala
                145                 150                 155 cca ggc cgc gcc aag acc ttc cgc ctg aag ctg ccc gcg ctg ctg gcg         529
Pro Gly Arg Ala Lys Thr Phe Arg Leu Lys Leu Pro Ala Leu Leu Ala
            160                 165                 170 ctg acg gcc cgg gag tcg tcg gtg cgg tcg ggc ggc gcg ggc ggc gcg         577
Leu Thr Ala Arg Glu Ser Ser Val Arg Ser Gly Gly Ala Gly Gly Ala
        175                 180                 185 ggc gcc ccg ggg gcc gtg gtg gtg gac gtg gac ctg acg ccc gcg gca         625
Gly Ala Pro Gly Ala Val Val Val Asp Val Asp Leu Thr Pro Ala Ala
    190                 195                 200 ccc agc agc gag tcg ctg gcc ctg gac gaa gtg aca gcc atg gac aac         673
Pro Ser Ser Glu Ser Leu Ala Leu Asp Glu Val Thr Ala Met Asp Asn
205                 210                 215                 220 cac gtg gca ggg ctc ggg ccc gcg gag gag cgg cgt gcg ctg gtg ggt         721
His Val Ala Gly Leu Gly Pro Ala Glu Glu Arg Arg Ala Leu Val Gly
                225                 230                 235 ccc ggc tct ccg ccc cgc agc gcg ccc ggc cag ctc cca tcg ccc cgg         769
Pro Gly Ser Pro Pro Arg Ser Ala Pro Gly Gln Leu Pro Ser Pro Arg
            240                 245                 250
```

|   |   |
|---|---|
| gcg cac agc ctc aac ccc gac gcc tcg ggc tcc agc tgc agc ctg gcc<br>Ala His Ser Leu Asn Pro Asp Ala Ser Gly Ser Ser Cys Ser Leu Ala<br>255                           260                           265 | 817 |
| cgg acg cgc tcc cga gaa agc tgc gcc agc gtg cgc gcc tcg tcg<br>Arg Thr Arg Ser Arg Glu Ser Cys Ala Ser Val Arg Arg Ala Ser Ser<br>   270                          275                      280 | 865 |
| gcc gac gac atc gag gcc atg cgc gcc ggg gtg ctg ccc ccg cca ccg<br>Ala Asp Asp Ile Glu Ala Met Arg Ala Gly Val Leu Pro Pro Pro Pro<br>285                           290                     295                    300 | 913 |
| cgc cac gcc agc acc ggg gcc atg cac cca ctg cgc agc ggt tg ctc<br>Arg His Ala Ser Thr Gly Ala Met His Pro Leu Arg Ser Gly Leu Leu<br>                   305                       310                     315 | 961 |
| aac tcc acc tcg gac tcc gac ctc gtg cgc tac cgc acc att agc aag<br>Asn Ser Thr Ser Asp Ser Asp Leu Val Arg Tyr Arg Thr Ile Ser Lys<br>320                           325                         330 | 1009 |
| att ccc caa atc acc ctc aac ttt gtg gac ctc aag ggc gac ccc ttc<br>Ile Pro Gln Ile Thr Leu Asn Phe Val Asp Leu Lys Gly Asp Pro Phe<br>                   335                       340                     345 | 1057 |
| ttg gct tcg ccc acc agt gac cgt gag atc ata gca cct aag ata aag<br>Leu Ala Ser Pro Thr Ser Asp Arg Glu Ile Ile Ala Pro Lys Ile Lys<br>350                           355                     360 | 1105 |
| gag cga acc cac aat gtc act gag aag gtc acc cag gtc ctg tcc ctg<br>Glu Arg Thr His Asn Val Thr Glu Lys Val Thr Gln Val Leu Ser Leu<br>365                           370                     375                   380 | 1153 |
| ggc gcc gac gtg ctg cct gag tac aag ctg cag gca ccg cgc atc cac<br>Gly Ala Asp Val Leu Pro Glu Tyr Lys Leu Gln Ala Pro Arg Ile His<br>                           385                     390                    395 | 1201 |
| cgc tgg acc atc ctg cat tac agc ccc ttc aag gcc gtg tgg gac tgg<br>Arg Trp Thr Ile Leu His Tyr Ser Pro Phe Lys Ala Val Trp Asp Trp<br>                   400                       405                     410 | 1249 |
| ctc atc ctg ctg ctg gtc atc tac acg gct gtc ttc aca ccc tac tcg<br>Leu Ile Leu Leu Leu Val Ile Tyr Thr Ala Val Phe Thr Pro Tyr Ser<br>                     415                      420                     425 | 1297 |
| gct gcc ttc ctg ctg aag gag acg gaa gaa ggc ccg cct gct acc gag<br>Ala Ala Phe Leu Leu Lys Glu Thr Glu Glu Gly Pro Pro Ala Thr Glu<br>430                           435                     440 | 1345 |
| tgt ggc tac gcc tgc cag ccg ctg gct gtg gtg gac ctc atc gtg gac<br>Cys Gly Tyr Ala Cys Gln Pro Leu Ala Val Val Asp Leu Ile Val Asp<br>445                           450                     455                    460 | 1393 |
| atc atg ttc att gtg gac atc ctc atc aac ttc cgc acc acc tac gtc<br>Ile Met Phe Ile Val Asp Ile Leu Ile Asn Phe Arg Thr Thr Tyr Val<br>                           465                     470                    475 | 1441 |
| aat gcc aac gag gag gtg gtc agc cac ccc ggc cgc atc gcc gtc cac<br>Asn Ala Asn Glu Glu Val Val Ser His Pro Gly Arg Ile Ala Val His<br>                   480                       485                     490 | 1489 |
| tac ttc aag ggc tgg ttc ctc atc gac atg gtg gcc gcc atc ccc ttc<br>Tyr Phe Lys Gly Trp Phe Leu Ile Asp Met Val Ala Ala Ile Pro Phe<br>                     495                      500                    505 | 1537 |
| gac ctg ctc atc ttc ggc tct ggc tct gag gag ctg atc ggg ctg ctg<br>Asp Leu Leu Ile Phe Gly Ser Gly Ser Glu Glu Leu Ile Gly Leu Leu<br>                   510                       515                    520 | 1585 |
| aag act gcg cgg ctg ctg cgg ctg gtg cgc gtg gcg cgg aag ctg gat<br>Lys Thr Ala Arg Leu Leu Arg Leu Val Arg Val Ala Arg Lys Leu Asp<br>525                           530                     535                    540 | 1633 |
| cgc tac tca gag tac ggc gcg gcc gtg ctg ttc ttg ctc atg tgc acc<br>Arg Tyr Ser Glu Tyr Gly Ala Ala Val Leu Phe Leu Leu Met Cys Thr<br>                   545                       550                     555 | 1681 |
| ttt gcg ctc atc gcg cac tgg cta gcc tgc atc tgg tac gcc atc ggc<br>Phe Ala Leu Ile Ala His Trp Leu Ala Cys Ile Trp Tyr Ala Ile Gly<br>                           560                      565                    570 | 1729 |

```
aac atg gag cag cca cac atg gac tca cgc atc ggc tgg ctg cac aac        1777
Asn Met Glu Gln Pro His Met Asp Ser Arg Ile Gly Trp Leu His Asn
        575                 580                 585 ctg ggc gac cag ata ggc aaa ccc tac aac agc agc ggc ctg ggc ggc        1825
Leu Gly Asp Gln Ile Gly Lys Pro Tyr Asn Ser Ser Gly Leu Gly Gly
    590                 595                 600 ccc tcc atc aag gac aag tat gtg acg gcg ctc tac ttc acc ttc agc        1873
Pro Ser Ile Lys Asp Lys Tyr Val Thr Ala Leu Tyr Phe Thr Phe Ser
605                 610                 615                 620 agc ctc acc agt gtg ggc ttc ggc aac gtc tct ccc aac acc aac tca        1921
Ser Leu Thr Ser Val Gly Phe Gly Asn Val Ser Pro Asn Thr Asn Ser
                625                 630                 635 gag aag atc ttc tcc atc tgc gtc atg ctc att ggc tcc ctc atg tat        1969
Glu Lys Ile Phe Ser Ile Cys Val Met Leu Ile Gly Ser Leu Met Tyr
            640                 645                 650 gct agc atc ttc ggc aac gtg tcg gcc atc atc cag cgg ctg tac tcg        2017
Ala Ser Ile Phe Gly Asn Val Ser Ala Ile Ile Gln Arg Leu Tyr Ser
        655                 660                 665 ggc aca gcc cgc tac cac aca cag atg ctg cgg gtg cgg gag ttc atc        2065
Gly Thr Ala Arg Tyr His Thr Gln Met Leu Arg Val Arg Glu Phe Ile
    670                 675                 680 cgc ttc cac cag atc ccc aat ccc ctg cgc cag cgc ctc gag gag tac        2113
Arg Phe His Gln Ile Pro Asn Pro Leu Arg Gln Arg Leu Glu Glu Tyr
685                 690                 695                 700 ttc cag cac gcc tgg tcc tac acc aac ggc atc gac atg aac gcg gtg        2161
Phe Gln His Ala Trp Ser Tyr Thr Asn Gly Ile Asp Met Asn Ala Val
                705                 710                 715 ctg aag ggc ttc cct gag tgc ctg cag gct gac atc tgc ctg cac ctg        2209
Leu Lys Gly Phe Pro Glu Cys Leu Gln Ala Asp Ile Cys Leu His Leu
            720                 725                 730 aac cgc tca ctg ctg cag cac tgc aaa ccc ttc cga ggg gcc acc aag        2257
Asn Arg Ser Leu Leu Gln His Cys Lys Pro Phe Arg Gly Ala Thr Lys
        735                 740                 745 ggc tgc ctt cgg gcc ctg gcc atg aag ttc aag acc aca cat gca ccg        2305
Gly Cys Leu Arg Ala Leu Ala Met Lys Phe Lys Thr Thr His Ala Pro
    750                 755                 760 cca ggg gac aca ctg gtg cat gct ggg gac ctg ctc acc gcc ctg tac        2353
Pro Gly Asp Thr Leu Val His Ala Gly Asp Leu Leu Thr Ala Leu Tyr
765                 770                 775                 780 ttc atc tcc cgg ggc tcc atc gag atc ctg cgg ggc gac gtc gtc gtg        2401
Phe Ile Ser Arg Gly Ser Ile Glu Ile Leu Arg Gly Asp Val Val Val
                785                 790                 795 gcc atc ctg ggg aag aat gac atc ttt ggg gag cct ctg aac ctg tat        2449
Ala Ile Leu Gly Lys Asn Asp Ile Phe Gly Glu Pro Leu Asn Leu Tyr
            800                 805                 810 gca agg cct ggc aag tcg aac ggg gat gtg cgg gcc ctc acc tac tgt        2497
Ala Arg Pro Gly Lys Ser Asn Gly Asp Val Arg Ala Leu Thr Tyr Cys
        815                 820                 825 gac cta cac aag atc cat cgg gac gac ctg ctg gag gtg ctg gac atg        2545
Asp Leu His Lys Ile His Arg Asp Asp Leu Leu Glu Val Leu Asp Met
    830                 835                 840 tac cct gag ttc tcc gac cac ttc tgg tcc agc ctg gag atc acc ttc        2593
Tyr Pro Glu Phe Ser Asp His Phe Trp Ser Ser Leu Glu Ile Thr Phe
845                 850                 855                 860 aac ctg cga gat acc aac atg atc ccg ggc tcc ccc ggc agt acg gag        2641
Asn Leu Arg Asp Thr Asn Met Ile Pro Gly Ser Pro Gly Ser Thr Glu
                865                 870                 875 tta gag ggt ggc ttc agt cgg caa cgc aag cgc aag ttg tcc ttc cgc        2689
Leu Glu Gly Gly Phe Ser Arg Gln Arg Lys Arg Lys Leu Ser Phe Arg
            880                 885                 890
```

```
agg cgc acg gac aag gac acg gag cag cca ggg gag gtg tcg gcc ttg   2737
Arg Arg Thr Asp Lys Asp Thr Glu Gln Pro Gly Glu Val Ser Ala Leu
            895                 900                 905 ggg ccg ggc cgg gcg ggg gca ggg ccg agt agc cgg ggc cgg ccg ggg   2785
Gly Pro Gly Arg Ala Gly Ala Gly Pro Ser Ser Arg Gly Arg Pro Gly
    910                 915                 920 ggg ccg tgg ggg gag agc ccg tcc agt ggc ccc tcc agc cct gag agc   2833
Gly Pro Trp Gly Glu Ser Pro Ser Ser Gly Pro Ser Ser Pro Glu Ser
925                 930                 935                 940 agt gag gat gag ggc cca ggc cgc agc tcc agc ccc ctc cgc ctg gtg   2881
Ser Glu Asp Glu Gly Pro Gly Arg Ser Ser Ser Pro Leu Arg Leu Val
                945                 950                 955 ccc ttc tcc agc ccc agg ccc ccc gga gag ccg ccg ggt ggg gag ccc   2929
Pro Phe Ser Ser Pro Arg Pro Pro Gly Glu Pro Pro Gly Gly Glu Pro
            960                 965                 970 ctg atg gag gac tgc gag aag agc agc gac act tgc aac ccc ctg tca   2977
Leu Met Glu Asp Cys Glu Lys Ser Ser Asp Thr Cys Asn Pro Leu Ser
        975                 980                 985 ggc gcc ttc tca gga gtg tcc aac att ttc agc ttc tgg ggg gac agt   3025
Gly Ala Phe Ser Gly Val Ser Asn Ile Phe Ser Phe Trp Gly Asp Ser
    990                 995                 1000 cgg ggc cgc cag tac cag gag ctc cct cga tgc ccc gcc ccc acc       3070
Arg Gly Arg Gln Tyr Gln Glu Leu Pro Arg Cys Pro Ala Pro Thr
1005                1010                1015 ccc agc ctc ctc aac atc ccc ctc tcc agc ccg ggt cgg cgg ccc       3115
Pro Ser Leu Leu Asn Ile Pro Leu Ser Ser Pro Gly Arg Arg Pro
1020                1025                1030 cgg ggc gac gtg gag agc agg ctg gat gcc ctc cag cgc cag ctc       3160
Arg Gly Asp Val Glu Ser Arg Leu Asp Ala Leu Gln Arg Gln Leu
1035                1040                1045 aac agg ctg gag acc cgg ctg agt gca gac atg gcc act gtc ctg       3205
Asn Arg Leu Glu Thr Arg Leu Ser Ala Asp Met Ala Thr Val Leu
1050                1055                1060 cag ctg cta cag agg cag atg acg ctg gtc ccg ccc gcc tac agt       3250
Gln Leu Leu Gln Arg Gln Met Thr Leu Val Pro Pro Ala Tyr Ser
1065                1070                1075 gct gtg acc acc ccg ggg cct ggc ccc act tcc aca tcc ccg ctg       3295
Ala Val Thr Thr Pro Gly Pro Gly Pro Thr Ser Thr Ser Pro Leu
1080                1085                1090 ttg ccc gtc agc ccc ctc ccc acc ctc acc ttg gac tcg ctt tct       3340
Leu Pro Val Ser Pro Leu Pro Thr Leu Thr Leu Asp Ser Leu Ser
1095                1100                1105 cag gtt tcc cag ttc atg gcg tgt gag gag ctg ccc ccg ggg gcc       3385
Gln Val Ser Gln Phe Met Ala Cys Glu Glu Leu Pro Pro Gly Ala
1110                1115                1120 cca gag ctt ccc caa gaa ggc ccc aca cga cgc ctc tcc cta ccg       3430
Pro Glu Leu Pro Gln Glu Gly Pro Thr Arg Arg Leu Ser Leu Pro
1125                1130                1135 ggc cag ctg ggg gcc ctc acc tcc cag ccc ctg cac aga cac ggc       3475
Gly Gln Leu Gly Ala Leu Thr Ser Gln Pro Leu His Arg His Gly
1140                1145                1150 tcg gac ccg ggc agt tag tggggctgcc cagtgtggac acgtggctca          3523
Ser Asp Pro Gly Ser
1155 cccagggatc aaggcgctgc tgggccgctc cccttggagg ccctgctcag gaggccctga  3583 ccgtggaagg ggagaggaac tcgaaagcac agctcctccc ccagcccttg ggaccatctt  3643 ctcctgcagt ccctgggcc  ccagtgagag gggcagggc  agggccggca gtaggtgggg   3703 cctgtggtcc cccactgcc  ctgagggcat tagctggtct aactgccgg  aggcacccgg   3763
```

```
cctgggcct  taggcacctc  aaggactttt  ctgctattta  ctgctcttat  tgttaaggat    3823
aataattaag  gatcatatga  ataattaatg  aagatgctga  tgactatgaa  taataaataa    3883
ttatcctgag  gagaaaa                                                      3900
```

<210> SEQ ID NO 2
<211> LENGTH: 1159
<212> TYPE: PRT
<213> ORGANISM: Homo sapiens

<400> SEQUENCE: 2

```
Met Pro Val Arg Arg Gly His Val Ala Pro Gln Asn Thr Phe Leu Asp
1               5                   10                  15

Thr Ile Ile Arg Lys Phe Glu Gly Gln Ser Arg Lys Phe Ile Ile Ala
            20                  25                  30

Asn Ala Arg Val Glu Asn Cys Ala Val Ile Tyr Cys Asn Asp Gly Phe
        35                  40                  45

Cys Glu Leu Cys Gly Tyr Ser Arg Ala Glu Val Met Gln Arg Pro Cys
    50                  55                  60

Thr Cys Asp Phe Leu His Gly Pro Arg Thr Gln Arg Arg Ala Ala Ala
65                  70                  75                  80

Gln Ile Ala Gln Ala Leu Leu Gly Ala Glu Glu Arg Lys Val Glu Ile
                85                  90                  95

Ala Phe Tyr Arg Lys Asp Gly Ser Cys Phe Leu Cys Leu Val Asp Val
            100                 105                 110

Val Pro Val Lys Asn Glu Asp Gly Ala Val Ile Met Phe Ile Leu Asn
        115                 120                 125

Phe Glu Val Val Met Glu Lys Asp Met Val Gly Ser Pro Ala His Asp
130                 135                 140

Thr Asn His Arg Gly Pro Pro Thr Ser Trp Leu Ala Pro Gly Arg Ala
145                 150                 155                 160

Lys Thr Phe Arg Leu Lys Leu Pro Ala Leu Leu Ala Leu Thr Ala Arg
                165                 170                 175

Glu Ser Ser Val Arg Ser Gly Gly Ala Gly Gly Ala Gly Ala Pro Gly
            180                 185                 190

Ala Val Val Val Asp Val Asp Leu Thr Pro Ala Ala Pro Ser Ser Glu
        195                 200                 205

Ser Leu Ala Leu Asp Glu Val Thr Ala Met Asp Asn His Val Ala Gly
210                 215                 220

Leu Gly Pro Ala Glu Glu Arg Arg Ala Leu Val Gly Pro Gly Ser Pro
225                 230                 235                 240

Pro Arg Ser Ala Pro Gly Gln Leu Pro Ser Pro Arg Ala His Ser Leu
                245                 250                 255

Asn Pro Asp Ala Ser Gly Ser Ser Cys Ser Leu Ala Arg Thr Arg Ser
            260                 265                 270

Arg Glu Ser Cys Ala Ser Val Arg Arg Ala Ser Ser Ala Asp Asp Ile
        275                 280                 285

Glu Ala Met Arg Ala Gly Val Leu Pro Pro Pro Arg His Ala Ser
290                 295                 300

Thr Gly Ala Met His Pro Leu Arg Ser Gly Leu Leu Asn Ser Thr Ser
305                 310                 315                 320

Asp Ser Asp Leu Val Arg Tyr Arg Thr Ile Ser Lys Ile Pro Gln Ile
                325                 330                 335

Thr Leu Asn Phe Val Asp Leu Lys Gly Asp Pro Phe Leu Ala Ser Pro
            340                 345                 350
```

-continued

```
Thr Ser Asp Arg Glu Ile Ile Ala Pro Lys Ile Lys Glu Arg Thr His
        355                 360                 365
Asn Val Thr Glu Lys Val Thr Gln Val Leu Ser Leu Gly Ala Asp Val
        370                 375                 380
Leu Pro Glu Tyr Lys Leu Gln Ala Pro Arg Ile His Arg Trp Thr Ile
385                 390                 395                 400
Leu His Tyr Ser Pro Phe Lys Ala Val Trp Asp Trp Leu Ile Leu Leu
                405                 410                 415
Leu Val Ile Tyr Thr Ala Val Phe Thr Pro Tyr Ser Ala Ala Phe Leu
                420                 425                 430
Leu Lys Glu Thr Glu Glu Gly Pro Ala Thr Glu Cys Gly Tyr Ala
        435                 440                 445
Cys Gln Pro Leu Ala Val Val Asp Leu Ile Val Asp Ile Met Phe Ile
        450                 455                 460
Val Asp Ile Leu Ile Asn Phe Arg Thr Thr Tyr Val Asn Ala Asn Glu
465                 470                 475                 480
Glu Val Val Ser His Pro Gly Arg Ile Ala Val His Tyr Phe Lys Gly
                485                 490                 495
Trp Phe Leu Ile Asp Met Val Ala Ala Ile Pro Phe Asp Leu Leu Ile
                500                 505                 510
Phe Gly Ser Gly Ser Glu Glu Leu Ile Gly Leu Leu Lys Thr Ala Arg
        515                 520                 525
Leu Leu Arg Leu Val Arg Val Ala Arg Lys Leu Asp Arg Tyr Ser Glu
        530                 535                 540
Tyr Gly Ala Ala Val Leu Phe Leu Leu Met Cys Thr Phe Ala Leu Ile
545                 550                 555                 560
Ala His Trp Leu Ala Cys Ile Trp Tyr Ala Ile Gly Asn Met Glu Gln
                565                 570                 575
Pro His Met Asp Ser Arg Ile Gly Trp Leu His Asn Leu Gly Asp Gln
                580                 585                 590
Ile Gly Lys Pro Tyr Asn Ser Ser Gly Leu Gly Gly Pro Ser Ile Lys
        595                 600                 605
Asp Lys Tyr Val Thr Ala Leu Tyr Phe Thr Phe Ser Ser Leu Thr Ser
        610                 615                 620
Val Gly Phe Gly Asn Val Ser Pro Asn Thr Asn Ser Glu Lys Ile Phe
625                 630                 635                 640
Ser Ile Cys Val Met Leu Ile Gly Ser Leu Met Tyr Ala Ser Ile Phe
                645                 650                 655
Gly Asn Val Ser Ala Ile Ile Gln Arg Leu Tyr Ser Gly Thr Ala Arg
                660                 665                 670
Tyr His Thr Gln Met Leu Arg Val Arg Glu Phe Ile Arg Phe His Gln
        675                 680                 685
Ile Pro Asn Pro Leu Arg Gln Arg Leu Glu Glu Tyr Phe Gln His Ala
        690                 695                 700
Trp Ser Tyr Thr Asn Gly Ile Asp Met Asn Ala Val Leu Lys Gly Phe
705                 710                 715                 720
Pro Glu Cys Leu Gln Ala Asp Ile Cys Leu His Leu Asn Arg Ser Leu
                725                 730                 735
Leu Gln His Cys Lys Pro Phe Arg Gly Ala Thr Lys Gly Cys Leu Arg
                740                 745                 750
Ala Leu Ala Met Lys Phe Lys Thr Thr His Ala Pro Pro Gly Asp Thr
        755                 760                 765
```

```
Leu Val His Ala Gly Asp Leu Leu Thr Ala Leu Tyr Phe Ile Ser Arg
    770                 775                 780

Gly Ser Ile Glu Ile Leu Arg Gly Asp Val Val Ala Ile Leu Gly
785                 790                 795                 800

Lys Asn Asp Ile Phe Gly Glu Pro Leu Asn Leu Tyr Ala Arg Pro Gly
                    805                 810                 815

Lys Ser Asn Gly Asp Val Arg Ala Leu Thr Tyr Cys Asp Leu His Lys
                820                 825                 830

Ile His Arg Asp Asp Leu Leu Glu Val Leu Asp Met Tyr Pro Glu Phe
                835                 840                 845

Ser Asp His Phe Trp Ser Ser Leu Glu Ile Thr Phe Asn Leu Arg Asp
    850                 855                 860

Thr Asn Met Ile Pro Gly Ser Pro Gly Ser Thr Glu Leu Glu Gly Gly
865                 870                 875                 880

Phe Ser Arg Gln Arg Lys Arg Lys Leu Ser Phe Arg Arg Thr Asp
                885                 890                 895

Lys Asp Thr Glu Gln Pro Gly Glu Val Ser Ala Leu Gly Pro Gly Arg
                900                 905                 910

Ala Gly Ala Gly Pro Ser Ser Arg Gly Arg Pro Gly Pro Trp Gly
                915                 920                 925

Glu Ser Pro Ser Ser Gly Pro Ser Pro Glu Ser Ser Asp Glu
    930                 935                 940

Gly Pro Gly Arg Ser Ser Ser Pro Leu Arg Leu Val Pro Phe Ser Ser
945                 950                 955                 960

Pro Arg Pro Pro Gly Glu Pro Gly Gly Glu Pro Leu Met Glu Asp
                965                 970                 975

Cys Glu Lys Ser Ser Asp Thr Cys Asn Pro Leu Ser Gly Ala Phe Ser
                980                 985                 990

Gly Val Ser Asn Ile Phe Ser Phe Trp Gly Asp Ser Arg Gly Arg Gln
                995                 1000                1005

Tyr Gln Glu Leu Pro Arg Cys Pro Ala Pro Thr Pro Ser Leu Leu
    1010                1015                1020

Asn Ile Pro Leu Ser Ser Pro Gly Arg Arg Pro Arg Gly Asp Val
    1025                1030                1035

Glu Ser Arg Leu Asp Ala Leu Gln Arg Gln Leu Asn Arg Leu Glu
    1040                1045                1050

Thr Arg Leu Ser Ala Asp Met Ala Thr Val Leu Gln Leu Leu Gln
    1055                1060                1065

Arg Gln Met Thr Leu Val Pro Pro Ala Tyr Ser Ala Val Thr Thr
    1070                1075                1080

Pro Gly Pro Gly Pro Thr Ser Thr Ser Pro Leu Leu Pro Val Ser
    1085                1090                1095

Pro Leu Pro Thr Leu Thr Leu Asp Ser Leu Ser Gln Val Ser Gln
    1100                1105                1110

Phe Met Ala Cys Glu Glu Leu Pro Pro Gly Ala Pro Glu Leu Pro
    1115                1120                1125

Gln Glu Gly Pro Thr Arg Arg Leu Ser Leu Pro Gly Gln Leu Gly
    1130                1135                1140

Ala Leu Thr Ser Gln Pro Leu His Arg His Gly Ser Asp Pro Gly
    1145                1150                1155

Ser
```

-continued

```
<210> SEQ ID NO 3
<211> LENGTH: 3191
<212> TYPE: DNA
<213> ORGANISM: Homo sapiens
<220> FEATURE:
<221> NAME/KEY: CDS
<222> LOCATION: (325)..(2784)

<400> SEQUENCE: 3
```

| | | |
|---|---|---|
| ccggctggag gagctgaggt tccgagtgcg gccgctgctg ggctggcggg cgggcagagc | 60 |
| acggcaccct ggcagcaggg cccacgccac ggggccatgg gcagctcgag ccaggcaggc | 120 |
| tgctgcccac gcttactgcc agggtgaccc cagccctggg gccagccac aaccaccctg | 180 |
| gcttcatgcc aggggctgct ctggttgcca gtcggccagc ctcgggggtg cagcctgggc | 240 |
| tgggactgct gctggggtgc aggtgaggca gtggccgggc cctcaggccc cagggcaggc | 300 |

| | | | | | | | | | | | |
|---|---|---|---|---|---|---|---|---|---|---|---|
| aggctgcagg gagccaagtc ctcc | atg | gcg | gcc | cca | gcc | ggg | aag | gcg | agc | | 351 |
| | Met | Ala | Ala | Pro | Ala | Gly | Lys | Ala | Ser | | |
| | 1 | | | | 5 | | | | | | |

| agg | aca | ggg | gct | ctg | cgg | ccc | agg | gcc | cag | aaa | ggc | cgg | gtg | agg | cgg | 399 |
|---|---|---|---|---|---|---|---|---|---|---|---|---|---|---|---|---|
| Arg | Thr | Gly | Ala | Leu | Arg | Pro | Arg | Ala | Gln | Lys | Gly | Arg | Val | Arg | Arg | |
| 10 | | | | 15 | | | | | 20 | | | | | 25 | | |

| gcc | gtg | cgc | atc | tcc | agc | ctc | gtg | gcc | cag | gag | gtc | ctg | tcc | ctg | ggc | 447 |
|---|---|---|---|---|---|---|---|---|---|---|---|---|---|---|---|---|
| Ala | Val | Arg | Ile | Ser | Ser | Leu | Val | Ala | Gln | Glu | Val | Leu | Ser | Leu | Gly | |
| | | | 30 | | | | | 35 | | | | | 40 | | | |

| gcc | gac | gtg | ctg | cct | gag | tac | aag | ctg | cag | gca | ccg | cgc | atc | cac | cgc | 495 |
|---|---|---|---|---|---|---|---|---|---|---|---|---|---|---|---|---|
| Ala | Asp | Val | Leu | Pro | Glu | Tyr | Lys | Leu | Gln | Ala | Pro | Arg | Ile | His | Arg | |
| | | 45 | | | | | 50 | | | | | 55 | | | | |

| tgg | acc | atc | ctg | cat | tac | agc | ccc | ttc | aag | gcc | gtg | tgg | gac | tgg | ctc | 543 |
|---|---|---|---|---|---|---|---|---|---|---|---|---|---|---|---|---|
| Trp | Thr | Ile | Leu | His | Tyr | Ser | Pro | Phe | Lys | Ala | Val | Trp | Asp | Trp | Leu | |
| | 60 | | | | | 65 | | | | | 70 | | | | | |

| atc | ctg | ctg | ctg | gtc | atc | tac | acg | gct | gtc | ttc | aca | ccc | tac | tcg | gct | 591 |
|---|---|---|---|---|---|---|---|---|---|---|---|---|---|---|---|---|
| Ile | Leu | Leu | Leu | Val | Ile | Tyr | Thr | Ala | Val | Phe | Thr | Pro | Tyr | Ser | Ala | |
| 75 | | | | | 80 | | | | | 85 | | | | | | |

| gcc | ttc | ctg | ctg | aag | gag | acg | gaa | gaa | ggc | ccg | cct | gct | acc | gag | tgt | 639 |
|---|---|---|---|---|---|---|---|---|---|---|---|---|---|---|---|---|
| Ala | Phe | Leu | Leu | Lys | Glu | Thr | Glu | Glu | Gly | Pro | Pro | Ala | Thr | Glu | Cys | |
| 90 | | | | 95 | | | | | 100 | | | | | 105 | | |

| ggc | tac | gcc | tgc | cag | ccg | ctg | gct | gtg | gtg | gac | ctc | atc | gtg | gac | atc | 687 |
|---|---|---|---|---|---|---|---|---|---|---|---|---|---|---|---|---|
| Gly | Tyr | Ala | Cys | Gln | Pro | Leu | Ala | Val | Val | Asp | Leu | Ile | Val | Asp | Ile | |
| | | | 110 | | | | | 115 | | | | | 120 | | | |

| atg | ttc | att | gtg | gac | atc | ctc | atc | aac | ttc | cgc | acc | acc | tac | gtc | aat | 735 |
|---|---|---|---|---|---|---|---|---|---|---|---|---|---|---|---|---|
| Met | Phe | Ile | Val | Asp | Ile | Leu | Ile | Asn | Phe | Arg | Thr | Thr | Tyr | Val | Asn | |
| | | 125 | | | | | 130 | | | | | 135 | | | | |

| gcc | aac | gag | gag | gtg | gtc | agc | cac | ccc | ggc | cgc | atc | gcc | gtc | cac | tac | 783 |
|---|---|---|---|---|---|---|---|---|---|---|---|---|---|---|---|---|
| Ala | Asn | Glu | Glu | Val | Val | Ser | His | Pro | Gly | Arg | Ile | Ala | Val | His | Tyr | |
| | 140 | | | | | 145 | | | | | 150 | | | | | |

| ttc | aag | ggc | tgg | ttc | ctc | atc | gac | atg | gtg | gcc | gcc | atc | ccc | ttc | gac | 831 |
|---|---|---|---|---|---|---|---|---|---|---|---|---|---|---|---|---|
| Phe | Lys | Gly | Trp | Phe | Leu | Ile | Asp | Met | Val | Ala | Ala | Ile | Pro | Phe | Asp | |
| 155 | | | | | 160 | | | | | 165 | | | | | | |

| ctg | ctc | atc | ttc | ggc | tct | ggc | tct | gag | gag | ctg | atc | ggg | ctg | ctg | aag | 879 |
|---|---|---|---|---|---|---|---|---|---|---|---|---|---|---|---|---|
| Leu | Leu | Ile | Phe | Gly | Ser | Gly | Ser | Glu | Glu | Leu | Ile | Gly | Leu | Leu | Lys | |
| 170 | | | | | 175 | | | | | 180 | | | | | 185 | |

| act | gcg | cgg | ctg | ctg | cgg | ctg | gtg | cgc | gtg | gcg | cgg | aag | ctg | gat | cgc | 927 |
|---|---|---|---|---|---|---|---|---|---|---|---|---|---|---|---|---|
| Thr | Ala | Arg | Leu | Leu | Arg | Leu | Val | Arg | Val | Ala | Arg | Lys | Leu | Asp | Arg | |
| | | | 190 | | | | | 195 | | | | | 200 | | | |

| tac | tca | gag | tac | ggc | gcg | gcc | gtg | ctg | ttc | ttg | ctc | atg | tgc | acc | ttt | 975 |
|---|---|---|---|---|---|---|---|---|---|---|---|---|---|---|---|---|
| Tyr | Ser | Glu | Tyr | Gly | Ala | Ala | Val | Leu | Phe | Leu | Leu | Met | Cys | Thr | Phe | |
| | | 205 | | | | | 210 | | | | | 215 | | | | |

| gcg | ctc | atc | gcg | cac | tgg | cta | gcc | tgc | atc | tgg | tac | gcc | atc | ggc | aac | 1023 |
|---|---|---|---|---|---|---|---|---|---|---|---|---|---|---|---|---|
| Ala | Leu | Ile | Ala | His | Trp | Leu | Ala | Cys | Ile | Trp | Tyr | Ala | Ile | Gly | Asn | |
| | 220 | | | | | 225 | | | | | 230 | | | | | |

```
atg gag cag cca cac atg gac tca cgc atc ggc tgg ctg cac aac ctg      1071
Met Glu Gln Pro His Met Asp Ser Arg Ile Gly Trp Leu His Asn Leu
235                 240                 245 ggc gac cag ata ggc aaa ccc tac aac agc agc ggc ctg ggc ggc ccc      1119
Gly Asp Gln Ile Gly Lys Pro Tyr Asn Ser Ser Gly Leu Gly Gly Pro
250                 255                 260                 265 tcc atc aag gac aag tat gtg acg gcg ctc tac ttc acc ttc agc agc      1167
Ser Ile Lys Asp Lys Tyr Val Thr Ala Leu Tyr Phe Thr Phe Ser Ser
                270                 275                 280 ctc acc agt gtg ggc ttc ggc aac gtc tct ccc aac acc aac tca gag      1215
Leu Thr Ser Val Gly Phe Gly Asn Val Ser Pro Asn Thr Asn Ser Glu
            285                 290                 295 aag atc ttc tcc atc tgc gtc atg ctc att ggc tcc ctc atg tat gct      1263
Lys Ile Phe Ser Ile Cys Val Met Leu Ile Gly Ser Leu Met Tyr Ala
300                 305                 310 agc atc ttc ggc aac gtg tcg gcc atc atc cag cgg ctg tac tcg ggc      1311
Ser Ile Phe Gly Asn Val Ser Ala Ile Ile Gln Arg Leu Tyr Ser Gly
315                 320                 325 aca gcc cgc tac cac aca cag atg ctg cgg gtg cgg gag ttc atc cgc      1359
Thr Ala Arg Tyr His Thr Gln Met Leu Arg Val Arg Glu Phe Ile Arg
330                 335                 340                 345 ttc cac cag atc ccc aat ccc ctg cgc cag cgc ctc gag gag tac ttc      1407
Phe His Gln Ile Pro Asn Pro Leu Arg Gln Arg Leu Glu Glu Tyr Phe
                350                 355                 360 cag cac gcc tgg tcc tac acc aac ggc atc gac atg aac gcg gtg ctg      1455
Gln His Ala Trp Ser Tyr Thr Asn Gly Ile Asp Met Asn Ala Val Leu
            365                 370                 375 aag ggc ttc cct gag tgc ctg cag gct gac atc tgc ctg cac ctg aac      1503
Lys Gly Phe Pro Glu Cys Leu Gln Ala Asp Ile Cys Leu His Leu Asn
380                 385                 390 cgc tca ctg ctg cag cac tgc aaa ccc ttc cga ggg gcc acc aag ggc      1551
Arg Ser Leu Leu Gln His Cys Lys Pro Phe Arg Gly Ala Thr Lys Gly
395                 400                 405 tgc ctt cgg gcc ctg gcc atg aag ttc aag acc aca cat gca ccg cca      1599
Cys Leu Arg Ala Leu Ala Met Lys Phe Lys Thr Thr His Ala Pro Pro
410                 415                 420                 425 ggg gac aca ctg gtg cat gct ggg gac ctg ctc acc gcc ctg tac ttc      1647
Gly Asp Thr Leu Val His Ala Gly Asp Leu Leu Thr Ala Leu Tyr Phe
                430                 435                 440 atc tcc cgg ggc tcc atc gag atc ctg cgg ggc gac gtc gtc gtg gcc      1695
Ile Ser Arg Gly Ser Ile Glu Ile Leu Arg Gly Asp Val Val Val Ala
            445                 450                 455 atc ctg ggg aag aat gac atc ttt ggg gag cct ctg aac ctg tat gca      1743
Ile Leu Gly Lys Asn Asp Ile Phe Gly Glu Pro Leu Asn Leu Tyr Ala
460                 465                 470 agg cct ggc aag tcg aac ggg gat gtg cgg gcc ctc acc tac tgt gac      1791
Arg Pro Gly Lys Ser Asn Gly Asp Val Arg Ala Leu Thr Tyr Cys Asp
475                 480                 485 cta cac aag atc cat cgg gac gac ctg ctg gag gtg ctg gac atg tac      1839
Leu His Lys Ile His Arg Asp Asp Leu Leu Glu Val Leu Asp Met Tyr
490                 495                 500                 505 cct gag ttc tcc gac cac ttc tgg tcc agc ctg gag atc acc ttc aac      1887
Pro Glu Phe Ser Asp His Phe Trp Ser Ser Leu Glu Ile Thr Phe Asn
                510                 515                 520 ctg cga gat acc aac atg atc ccg ggc tcc ccc ggc agt acg gag tta      1935
Leu Arg Asp Thr Asn Met Ile Pro Gly Ser Pro Gly Ser Thr Glu Leu
            525                 530                 535 gag ggt ggc ttc agt cgg caa cgc aag cgc aag ttg tcc ttc cgc agg      1983
Glu Gly Gly Phe Ser Arg Gln Arg Lys Arg Lys Leu Ser Phe Arg Arg
540                 545                 550
```

```
                                               -continued
cgc acg gac aag gac acg gag cag cca ggg gag gtg tcg gcc ttg ggg       2031
Arg Thr Asp Lys Asp Thr Glu Gln Pro Gly Glu Val Ser Ala Leu Gly
555                 560                 565 ccg ggc cgg gcg ggg gca ggg ccg agt agc cgg ggc cgg ccg ggg ggg       2079
Pro Gly Arg Ala Gly Ala Gly Pro Ser Ser Arg Gly Arg Pro Gly Gly
570                 575                 580                 585 ccg tgg ggg gag agc ccg tcc agt ggc ccc tcc agc cct gag agc agt       2127
Pro Trp Gly Glu Ser Pro Ser Ser Gly Pro Ser Ser Pro Glu Ser Ser
                    590                 595                 600 gag gat gag ggc cca ggc cgc agc tcc agc ccc ctc cgc ctg gtg ccc       2175
Glu Asp Glu Gly Pro Gly Arg Ser Ser Ser Pro Leu Arg Leu Val Pro
                605                 610                 615 ttc tcc agc ccc agg ccc ccc gga gag ccg ccg ggt ggg gag ccc ctg       2223
Phe Ser Ser Pro Arg Pro Pro Gly Glu Pro Pro Gly Gly Glu Pro Leu
            620                 625                 630 atg gag gac tgc gag aag agc agc gac act tgc aac ccc ctg tca ggc       2271
Met Glu Asp Cys Glu Lys Ser Ser Asp Thr Cys Asn Pro Leu Ser Gly
635                 640                 645 gcc ttc tca gga gtg tcc aac att ttc agc ttc tgg ggg gac agt cgg       2319
Ala Phe Ser Gly Val Ser Asn Ile Phe Ser Phe Trp Gly Asp Ser Arg
650                 655                 660                 665 ggc cgc cag tac cag gag ctc cct cga tgc ccc gcc ccc acc ccc agc       2367
Gly Arg Gln Tyr Gln Glu Leu Pro Arg Cys Pro Ala Pro Thr Pro Ser
                670                 675                 680 ctc ctc aac atc ccc ctc tcc agc ccg ggt cgg cgg ccc cgg ggc gac       2415
Leu Leu Asn Ile Pro Leu Ser Ser Pro Gly Arg Arg Pro Arg Gly Asp
                685                 690                 695 gtg gag agc agg ctg gat gcc ctc cag cgc cag ctc aac agg ctg gag       2463
Val Glu Ser Arg Leu Asp Ala Leu Gln Arg Gln Leu Asn Arg Leu Glu
            700                 705                 710 acc cgg ctg agt gca gac atg gcc act gtc ctg cag ctg cta cag agg       2511
Thr Arg Leu Ser Ala Asp Met Ala Thr Val Leu Gln Leu Leu Gln Arg
715                 720                 725 cag atg acg ctg gtc ccg ccc gcc tac agt gct gtg acc acc ccg ggg       2559
Gln Met Thr Leu Val Pro Pro Ala Tyr Ser Ala Val Thr Thr Pro Gly
730                 735                 740                 745 cct ggc ccc act tcc aca tcc ccg ctg ttg ccc gtc agc ccc ctc ccc       2607
Pro Gly Pro Thr Ser Thr Ser Pro Leu Leu Pro Val Ser Pro Leu Pro
                750                 755                 760 acc ctc acc ttg gac tcg ctt tct cag gtt tcc cag ttc atg gcg tgt       2655
Thr Leu Thr Leu Asp Ser Leu Ser Gln Val Ser Gln Phe Met Ala Cys
                765                 770                 775 gag gag ctg ccc ccg ggg gcc cca gag ctt ccc caa gaa ggc ccc aca       2703
Glu Glu Leu Pro Pro Gly Ala Pro Glu Leu Pro Gln Glu Gly Pro Thr
            780                 785                 790 cga cgc ctc tcc cta ccg ggc cag ctg ggg gcc ctc acc tcc cag ccc       2751
Arg Arg Leu Ser Leu Pro Gly Gln Leu Gly Ala Leu Thr Ser Gln Pro
795                 800                 805 ctg cac aga cac ggc tcg gac ccg ggc agt tag tggggctgcc cagtgtggac    2804
Leu His Arg His Gly Ser Asp Pro Gly Ser
810                 815 acgtggctca cccagggatc aaggcgctgc tgggccgctc cccttggagg ccctgctcag   2864
gaggccctga ccgtggaagg ggagaggaac tcgaaagcac agctcctccc ccagcccttg   2924
ggaccatctt ctcctgcagt cccctggggcc ccagtgagag gggcaggggc agggccggca  2984
gtaggtgggg cctgtggtcc ccccactgcc ctgagggcat tagctggtct aactgcccgg   3044
aggcacccgg ccctgggcct taggcacctc aaggactttt ctgctattta ctgctcttat   3104
```

-continued

```
tgttaaggat aataattaag gatcatatga ataattaatg aagatgctga tgactatgaa    3164 taataaaataa ttatcctgag gagaaaa                                        3191
```

<210> SEQ ID NO 4
<211> LENGTH: 819
<212> TYPE: PRT
<213> ORGANISM: Homo sapiens

<400> SEQUENCE: 4

```
Met Ala Ala Pro Ala Gly Lys Ala Ser Arg Thr Gly Ala Leu Arg Pro
1               5                   10                  15

Arg Ala Gln Lys Gly Arg Val Arg Ala Val Arg Ile Ser Ser Leu
                20                  25                  30

Val Ala Gln Glu Val Leu Ser Leu Gly Ala Asp Val Leu Pro Glu Tyr
            35                  40                  45

Lys Leu Gln Ala Pro Arg Ile His Arg Trp Thr Ile Leu His Tyr Ser
        50                  55                  60

Pro Phe Lys Ala Val Trp Asp Trp Leu Ile Leu Leu Leu Val Ile Tyr
65                  70                  75                  80

Thr Ala Val Phe Thr Pro Tyr Ser Ala Ala Phe Leu Leu Lys Glu Thr
                85                  90                  95

Glu Glu Gly Pro Pro Ala Thr Glu Cys Gly Tyr Ala Cys Gln Pro Leu
            100                 105                 110

Ala Val Val Asp Leu Ile Val Asp Ile Met Phe Ile Val Asp Ile Leu
        115                 120                 125

Ile Asn Phe Arg Thr Thr Tyr Val Asn Ala Asn Glu Glu Val Val Ser
130                 135                 140

His Pro Gly Arg Ile Ala Val His Tyr Phe Lys Gly Trp Phe Leu Ile
145                 150                 155                 160

Asp Met Val Ala Ala Ile Pro Phe Asp Leu Leu Ile Phe Gly Ser Gly
                165                 170                 175

Ser Glu Glu Leu Ile Gly Leu Leu Lys Thr Ala Arg Leu Leu Arg Leu
            180                 185                 190

Val Arg Val Ala Arg Lys Leu Asp Arg Tyr Ser Glu Tyr Gly Ala Ala
        195                 200                 205

Val Leu Phe Leu Leu Met Cys Thr Phe Ala Leu Ile Ala His Trp Leu
    210                 215                 220

Ala Cys Ile Trp Tyr Ala Ile Gly Asn Met Glu Gln Pro His Met Asp
225                 230                 235                 240

Ser Arg Ile Gly Trp Leu His Asn Leu Gly Asp Gln Ile Gly Lys Pro
                245                 250                 255

Tyr Asn Ser Ser Gly Leu Gly Gly Pro Ser Ile Lys Asp Lys Tyr Val
            260                 265                 270

Thr Ala Leu Tyr Phe Thr Phe Ser Ser Leu Thr Ser Val Gly Phe Gly
        275                 280                 285

Asn Val Ser Pro Asn Thr Asn Ser Glu Lys Ile Phe Ser Ile Cys Val
    290                 295                 300

Met Leu Ile Gly Ser Leu Met Tyr Ala Ser Ile Phe Gly Asn Val Ser
305                 310                 315                 320

Ala Ile Ile Gln Arg Leu Tyr Ser Gly Thr Ala Arg Tyr His Thr Gln
                325                 330                 335

Met Leu Arg Val Arg Glu Phe Ile Arg Phe His Gln Ile Pro Asn Pro
            340                 345                 350
```

-continued

```
Leu Arg Gln Arg Leu Glu Glu Tyr Phe Gln His Ala Trp Ser Tyr Thr
        355                 360                 365

Asn Gly Ile Asp Met Asn Ala Val Leu Lys Gly Phe Pro Glu Cys Leu
    370                 375                 380

Gln Ala Asp Ile Cys Leu His Leu Asn Arg Ser Leu Leu Gln His Cys
385                 390                 395                 400

Lys Pro Phe Arg Gly Ala Thr Lys Gly Cys Leu Arg Ala Leu Ala Met
                405                 410                 415

Lys Phe Lys Thr Thr His Ala Pro Pro Gly Asp Thr Leu Val His Ala
            420                 425                 430

Gly Asp Leu Leu Thr Ala Leu Tyr Phe Ile Ser Arg Gly Ser Ile Glu
        435                 440                 445

Ile Leu Arg Gly Asp Val Val Ala Ile Leu Gly Lys Asn Asp Ile
    450                 455                 460

Phe Gly Glu Pro Leu Asn Leu Tyr Ala Arg Pro Gly Lys Ser Asn Gly
465                 470                 475                 480

Asp Val Arg Ala Leu Thr Tyr Cys Asp Leu His Lys Ile His Arg Asp
                485                 490                 495

Asp Leu Leu Glu Val Leu Asp Met Tyr Pro Glu Phe Ser Asp His Phe
            500                 505                 510

Trp Ser Ser Leu Glu Ile Thr Phe Asn Leu Arg Asp Thr Asn Met Ile
        515                 520                 525

Pro Gly Ser Pro Gly Ser Thr Glu Leu Glu Gly Gly Phe Ser Arg Gln
    530                 535                 540

Arg Lys Arg Lys Leu Ser Phe Arg Arg Thr Asp Lys Asp Thr Glu
545                 550                 555                 560

Gln Pro Gly Glu Val Ser Ala Leu Gly Pro Gly Arg Ala Gly Ala Gly
                565                 570                 575

Pro Ser Ser Arg Gly Arg Pro Gly Gly Pro Trp Gly Glu Ser Pro Ser
            580                 585                 590

Ser Gly Pro Ser Ser Pro Glu Ser Ser Glu Asp Glu Gly Pro Gly Arg
        595                 600                 605

Ser Ser Ser Pro Leu Arg Leu Val Pro Phe Ser Ser Pro Arg Pro Pro
    610                 615                 620

Gly Glu Pro Pro Gly Gly Glu Pro Leu Met Glu Asp Cys Glu Lys Ser
625                 630                 635                 640

Ser Asp Thr Cys Asn Pro Leu Ser Gly Ala Phe Ser Gly Val Ser Asn
                645                 650                 655

Ile Phe Ser Phe Trp Gly Asp Ser Arg Gly Arg Gln Tyr Gln Glu Leu
            660                 665                 670

Pro Arg Cys Pro Ala Pro Thr Pro Ser Leu Leu Asn Ile Pro Leu Ser
        675                 680                 685

Ser Pro Gly Arg Arg Pro Arg Gly Asp Val Glu Ser Arg Leu Asp Ala
    690                 695                 700

Leu Gln Arg Gln Leu Asn Arg Leu Glu Thr Arg Leu Ser Ala Asp Met
705                 710                 715                 720

Ala Thr Val Leu Gln Leu Leu Gln Arg Gln Met Thr Leu Val Pro Pro
                725                 730                 735

Ala Tyr Ser Ala Val Thr Thr Pro Gly Pro Gly Pro Thr Ser Thr Ser
            740                 745                 750

Pro Leu Leu Pro Val Ser Pro Leu Pro Thr Leu Thr Leu Asp Ser Leu
        755                 760                 765
```

```
Ser Gln Val Ser Gln Phe Met Ala Cys Glu Glu Leu Pro Pro Gly Ala
    770                 775                 780

Pro Glu Leu Pro Gln Glu Gly Pro Thr Arg Arg Leu Ser Leu Pro Gly
785                 790                 795                 800

Gln Leu Gly Ala Leu Thr Ser Gln Pro Leu His Arg His Gly Ser Asp
                805                 810                 815

Pro Gly Ser
```